US012629148B2

(12) United States Patent
Lee et al.

(10) Patent No.: US 12,629,148 B2
(45) Date of Patent: May 19, 2026

(54) SURGICAL INSTRUMENT

(71) Applicant: LIVSMED INC., Seongnam-si (KR)

(72) Inventors: Jung Joo Lee, Seongnam-si (KR); Woo Jung Choi, Siheung-si (KR)

(73) Assignee: LIVSMED INC., Seongnam-si (KR)

( * ) Notice: Subject to any disclaimer, the term of this patent is extended or adjusted under 35 U.S.C. 154(b) by 23 days.

(21) Appl. No.: 18/938,488

(22) Filed: Nov. 6, 2024

(65) Prior Publication Data

US 2025/0143695 A1     May 8, 2025

(30) Foreign Application Priority Data

Nov. 8, 2023     (KR) ......................... 10-2023-0153490

(51) Int. Cl.
      *A61B 17/072*       (2006.01)
      *A61B 17/00*        (2006.01)
      *A61B 17/068*       (2006.01)
(52) U.S. Cl.
      CPC ...... *A61B 17/068* (2013.01); *A61B 17/00234* (2013.01); *A61B 2017/00407* (2013.01); *A61B 2017/00477* (2013.01); *A61B 2017/00862* (2013.01); *A61B 2017/07278* (2013.01)
(58) Field of Classification Search
      CPC ............ A61B 17/07207; A61B 17/072; A61B 2017/00407; A61B 2017/00477; A61B 2017/320052; A61B 2017/00323; A61B 2017/2905
      See application file for complete search history.

(56) References Cited

U.S. PATENT DOCUMENTS

| | | | | |
|---|---|---|---|---|
| 5,762,256 A * | 6/1998 | Mastri | .................. | A61B 17/072 227/176.1 |
| 11,197,669 B2 * | 12/2021 | Park | ................. | A61B 17/07207 |
| 12,089,847 B2 * | 9/2024 | Lee | ..................... | A61B 17/2909 |
| 12,329,380 B2 * | 6/2025 | Lee | ................. | A61B 17/07207 |
| 12,349,903 B2 * | 7/2025 | Lee | ................. | A61B 17/07207 |
| 2012/0010616 A1 | 1/2012 | Huang et al. | | |
| 2021/0106327 A1 * | 4/2021 | Park | ..................... | A61B 17/072 |
| 2024/0197318 A1 * | 6/2024 | Lee | ................. | A61B 17/07207 |

FOREIGN PATENT DOCUMENTS

| | | | | |
|---|---|---|---|---|
| CN | 104434243 B | 8/2016 | | |
| EP | 1515651 B1 | 12/2006 | | |
| JP | 2014-508572 A | 4/2014 | | |
| KR | 10-2007-0079046 A | 8/2007 | | |
| WO | WO-2022225367 A1 * | 10/2022 | ....... | A61B 17/07207 |

* cited by examiner

*Primary Examiner* — Andrew M Tecco
(74) *Attorney, Agent, or Firm* — Bridgeway IP Law Group, PLLC; Sang Ho Lee; Hyun Woo Shin

(57)     ABSTRACT

A surgical instrument includes an end tool including one or more jaws, wherein one of the one or more jaws includes a reciprocating assembly disposed in the jaw and formed to be movable in a first direction, which is a longitudinal direction of jaw, an operation member formed to be in contact with the reciprocating assembly and movable forward toward a distal end of the jaw from a proximal end side of the jaw in the first direction by the reciprocating assembly, and a backward-moving wire disposed adjacent to the operation member and movable in the first direction, wherein the backward-moving wire includes one or more coupling members fixed to the backward-moving wire, wherein the one or more coupling members are allowed to move the operation member backward toward the proximal end of the jaw.

24 Claims, 36 Drawing Sheets

SURGICAL INSTRUMENT

CROSS-REFERENCE TO RELATED APPLICATION

This application is based on and claims priority under 35 USC § 119 to Korean Patent Application No. 10-2023-0153490, filed on Nov. 8, 2023, in the Korean Intellectual Property Office, the disclosure of which is incorporated by reference herein in its entirety.

BACKGROUND

1. Field

The present disclosure relates to a surgical instrument, and more particularly, to a surgical instrument capable of being mounted on a robot arm or operated manually for use in laparoscopic surgery or various surgeries.

2. Description of the Related Art

In recent years, laparoscopic surgery has been actively used to reduce postoperative recovery time and complications through small incisions. The laparoscopic surgery is a surgical method in which a plurality of small holes are drilled in the abdomen of a patient and the inside of the abdominal cavity is observed through these holes, and is widely used in general surgery and the like.

In performing the laparoscopic surgery, a suturing instrument inserted into the body is used to suture a surgical site in the abdominal cavity, and a surgical stapler for suturing the surgical site using medical staples is used as the suturing instrument.

In general, a surgical stapler is a medical instrument that is often used for cutting and anastomosis of an organ in abdominal and thoracic surgery. The surgical stapler includes an open stapler used in thoracotomy and laparotomy and an endo stapler used in thoracoscopic surgery and celioscopic surgery.

The surgical stapler has advantages of not only shortening operation time since cutting of a surgical site and anastomosis of an organ are simultaneously performed, but also accurately stapling the surgical site. In addition, the surgical stapler has advantages of a faster recovery and a smaller scar than those when tissue is cut and stapled using a surgical stapling thread, and thus has been widely used in modern surgical operations. In particular, the surgical stapler has been widely used in cancer surgery to cut cancer tissue and suture a cut site.

The aforementioned background technology is technical information possessed by the inventor for derivation of the present disclosure or acquired by the inventor during the derivation of the present disclosure, and is not necessarily prior art disclosed to the public before the application of the present disclosure.

SUMMARY

The present disclosure is directed to providing a surgical instrument, which may be mounted on a robot arm or operable manually to be used in laparoscopic surgery or other various surgeries, and have a mechanism preventing backward movement of an operation member during stapling and a backward-moving wire structure to facilitate the backward movement of the operation member after the stapling.

Additional aspects will be set forth in part in the description which follows and, in part, will be apparent from the description, or may be learned by practice of the presented embodiments of the disclosure.

According to an aspect of the present disclosure, there is provided a surgical instrument including an end tool having one or more jaws and formed to be rotatable in at least one direction, wherein one of the one or more jaws includes a reciprocating assembly disposed in the jaw and formed to be movable in a first direction, which is a longitudinal direction of jaw, with respect to the jaw, an operation member formed on one side of the reciprocating assembly, and formed to be in contact with the reciprocating assembly and movable forward toward a distal end of the jaw from a proximal end side of the jaw in the first direction by the reciprocating assembly, and a backward-moving wire disposed adjacent to the operation member and movable in the first direction, wherein the backward-moving wire includes one or more coupling members fixed to the backward-moving wire, wherein the coupling member is allowed to move the operation member backward toward the proximal end of the jaw while moving toward the proximal end of the jaw together with the backward-moving wire.

In an embodiment of the present disclosure, the jaw may further include a backward-moving wire pulley formed at the distal end of the jaw, wherein the backward-moving wire may be wound to make partial contact with the backward-moving wire pulley, and may emerge as two strands extending toward the proximal end.

In an embodiment of the present disclosure, the jaw may further include an auxiliary pulley disposed adjacent to the backward-moving wire pulley, wherein the auxiliary pulley may adjust a position or a distance between the two strands of the backward-moving wire, after which the backward-moving wire is disposed.

In an embodiment of the present disclosure, when the two strands of the backward-moving wire are divided into an inner side wire, which is one of the two strands and closer to the operation member, and an outer side wire, which is another one of the two strands, the coupling member may be coupled to the outer side wire.

In an embodiment of the present disclosure, the end tool may further include a jaw rotation shaft serving as a rotation center of the jaw, and a loop pulley to which the jaw rotation shaft is coupled and around which the backward-moving wire is wound to make partial contact.

In an embodiment of the present disclosure, the loop pulley may be configured with two independently rotatable pulleys, and the two strands of the backward-moving wire may be respectively wound around the loop pulleys in different directions with respect to the jaw rotation shaft.

In an embodiment of the present disclosure, the reciprocating assembly may have a plurality of recesses formed on at least one surface thereof, and the operation member may include a ratchet member having at least one surface on which a ratchet is formed, wherein the ratchet of the ratchet member may be formed to be in contact with each of the recesses of the reciprocating assembly.

In an embodiment of the present disclosure, the coupling member may come into contact with the ratchet member to move the operation member backward toward the proximal end.

In an embodiment of the present disclosure, the ratchet member may include a protrusion protruding from an opposite surface of the surface on which the ratchet is formed, and the coupling member may come into contact with the protrusion of the ratchet member.

In an embodiment of the present disclosure, a hollow may be formed in the protrusion of the ratchet member, and the backward-moving wire may pass through the protrusion through the hollow.

In an embodiment of the present disclosure, the backward-moving wire and the coupling member may be positioned on the opposite side of the reciprocating assembly with respect to the ratchet member.

In an embodiment of the present disclosure, the coupling member may be disposed on the distal end side to avoid interference with the operation member until the operation member moves forward to the end of the distal end of the jaw.

In an embodiment of the present disclosure, as the operation member moves forward toward the distal end, the coupling member may be moved together with the operation member at a front surface of the operation member while being spaced apart from the operation member to secure a clearance space.

According to another aspect of the present disclosure, there is provided a surgical instrument including an end tool having one or more jaws and formed to be rotatable in at least one direction, wherein one of the one or more jaws includes a reciprocating assembly disposed in the jaw and formed to be movable in a first direction, which is a longitudinal direction of jaw, with respect to the jaw, an operation member formed on one side of the reciprocating assembly, and formed to be in contact with the reciprocating assembly and movable forward toward a distal end of the jaw from a proximal end side of the jaw in the first direction by the reciprocating assembly, and a backward-moving wire disposed adjacent to the operation member and movable in the first direction, wherein the backward-moving wire includes one or more coupling members fixed to the backward-moving wire, and when the reciprocating assembly moves toward the proximal end of the jaw, the coupling member is brought into contact with the operation member to prevent the operation member from moving toward the proximal end of the jaw.

In an embodiment of the present disclosure, as the operation member moves forward toward the distal end, the coupling member may be moved together with the operation member at a rear surface of the operation member while being spaced apart from the operation member to secure a clearance space.

In an embodiment of the present disclosure, as the operation member moves forward toward the distal end, the coupling member may be moved together with the operation member at the rear surface of the operation member while applying a force to the operation member in a forward movement direction.

In an embodiment of the present disclosure, the operation member may include a protrusion protruding toward the backward-moving wire, wherein the coupling member may be disposed at the rear of the protrusion.

In an embodiment of the present disclosure, the reciprocating assembly may have a plurality of recesses formed on at least one surface thereof, and the operation member may include a ratchet member having at least one surface on which a ratchet is formed, wherein the ratchet of the ratchet member may be formed to be in contact with each of the recesses of the reciprocating assembly.

In an embodiment of the present disclosure, the coupling member may be disposed at the rear of the ratchet member.

In an embodiment of the present disclosure, a hollow may be formed in the protrusion of the ratchet member, and the backward-moving wire may pass through the protrusion through the hollow.

In an embodiment of the present disclosure, when the two strands of the backward-moving wire are divided into an inner side wire, which is one of the two strands and closer to the operation member, and an outer side wire, which is another one of the two strands, the coupling member may be coupled to the inner side wire.

In an embodiment of the present disclosure, the backward-moving wire may further include a backward-movement coupling member allowed to move the operation member backward toward the proximal end while moving toward the proximal end together with the backward-moving wire.

In an embodiment of the present disclosure, when two strands of the backward-moving wire are divided into an inner side wire, which is one of the two strands and closer to the operation member, and an outer side wire, which is another one of the two strands, the backward-movement coupling member and the coupling member may be both coupled to only one of the inner side wire and the outer side wire.

In an embodiment of the present disclosure, as the operation member moves forward toward the distal end, the backward-movement coupling member may be moved together with the operation member at a front surface of the operation member while being spaced apart from the operation member to secure a clearance space.

According to another aspect of the present disclosure, there is provided a surgical instrument including an end tool having one or more jaws and formed to be rotatable in at least one direction, wherein one of the one or more jaws includes a reciprocating assembly disposed in the jaw and formed to be movable in a first direction, which is a longitudinal direction of jaw, with respect to the jaw, and an operation member formed on one side of the reciprocating assembly, and formed to be in contact with the reciprocating assembly and movable forward toward a distal end of the jaw from a proximal end side of the jaw in the first direction by the reciprocating assembly, wherein one or more recesses are formed in a region of an inner side surface of the jaw, which is to be in contact with the operation member, and a snap to be in contact with each of the recesses is formed in the operation member.

In an embodiment of the present disclosure, when the reciprocating assembly moves toward the proximal end of the jaw, the snap may be brought into contact with the recess to prevent the operation member from moving toward the proximal end of the jaw.

In an embodiment of the present disclosure, one end portion of the snap may be coupled to the operation member and is formed to be elastically deformable to a certain extent.

In an embodiment of the present disclosure, the recesses may be formed below a movement path of the operation member, one end portion of the snap may be coupled to a lower end of a rear surface of the operation member, and another end portion of the snap may be in contact with each of the recesses.

In an embodiment of the present disclosure, each of the one or more recesses may include an inclined surface formed to have a greater height at the distal end side of the jaw than the proximal end side of the jaw.

In an embodiment of the present disclosure, each of the one or more recesses may include a first inclined surface, which is a surface at the proximal end side, and a second inclined surface, which is a surface of the distal end side, wherein the first inclined surface may be formed to have a gentle slope, and the second inclined surface may be formed to be near vertical.

In an embodiment of the present disclosure, when the operation member moves forward toward the distal end, the snap may be moved up along the first inclined surface and moved toward the distal end, and when the reciprocating assembly moves backward to the proximal end, the snap may interfere with the second inclined surface to prevent the operation member from moving backward toward the proximal end.

In an embodiment of the present disclosure, the surgical instrument may further include a backward-moving wire allowed to move the operation member backward toward the proximal end, wherein, when the operation member is moved backward to the proximal end by the backward-moving wire, the snap may be plastically deformed and may lose a function thereof to prevent the backward movement of the operation member.

Other aspects, features, and advantages other than those described above will become apparent from the following drawings, claims, and detailed description of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
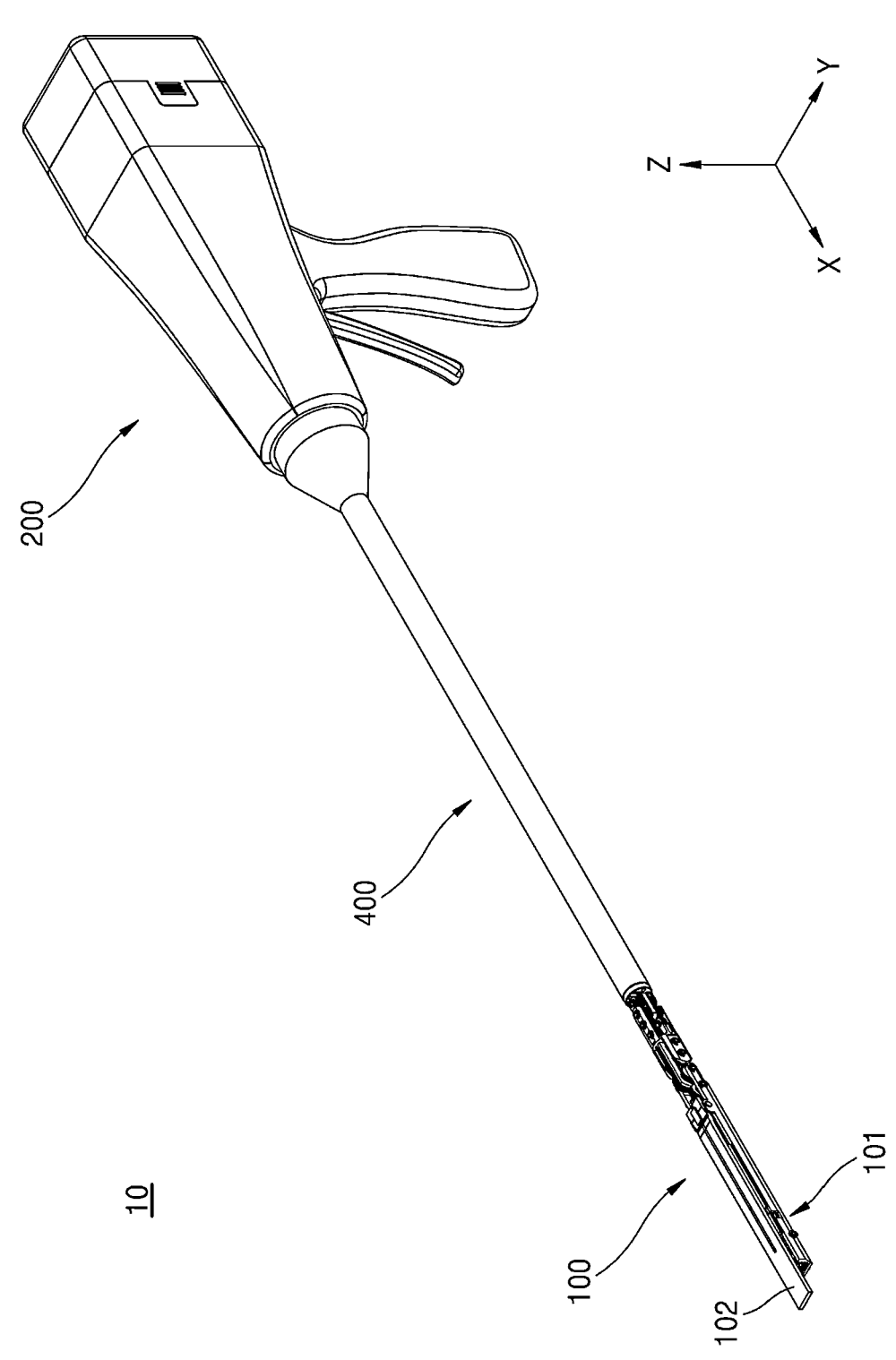
FIG. 1 is a perspective view illustrating a surgical instrument according to a first embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Hereinafter, the following embodiments will be described in detail with reference to the accompanying drawings. When describing with reference to the drawings, identical or corresponding components will be assigned the same reference numerals and duplicate descriptions thereof will be omitted.

Since various transformations can be made to these embodiments, specific embodiments will be illustrated in the drawings and described in detail in the detailed description. The effects and features of the present embodiments and the accompanying methods thereof will become apparent from the following description of the contents, taken in conjunction with the accompanying drawings. However, the present embodiments are not limited to the embodiments disclosed below, but may be implemented in various forms.

In describing the present disclosure, detailed description of known related arts will be omitted when it is determined that the gist of the present disclosure may be unnecessarily obscured.

In the following embodiments, singular forms are intended to include plural forms as well, unless the context clearly indicates otherwise. Although terms such as "first," "second," and the like may be used to describe various components, such components should not be limited to the above terms. The terms are only used to distinguish one component from another.

In the following embodiments, terms such as "include" or "have" means that the features or components described in the specification are present, and the possibility that one or more other features or components will be added is not excluded in advance.

In the following embodiments, when a unit, region, or component is referred to as being formed on another unit, region, or component, it can be directly formed on the other unit, region, or component. That is, for example, intervening units, regions, or components may be present.

In the following embodiments, terms such as "connecting" or "coupling" two members do not necessarily mean a direct and/or fixed connection or coupling of the two members, unless the context clearly indicates otherwise, and do not preclude another members from being interposed between the two members.

Sizes of components in the drawings may be exaggerated or reduced for convenience of description. For example, since the size and thickness of each component shown in the drawings are arbitrarily illustrated for convenience of description, the following embodiments are not necessarily limited thereto.

First Embodiment of Surgical Instrument

Figure 2:
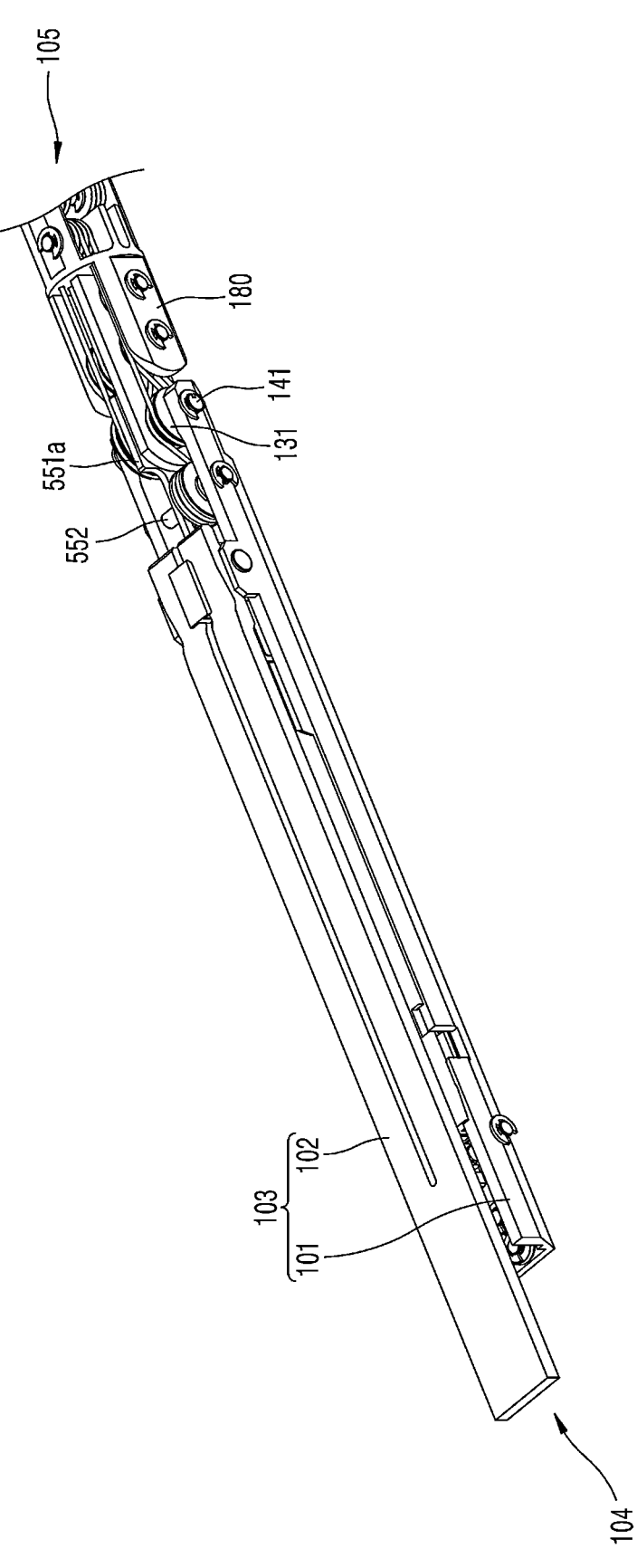
FIG. 2 is a perspective view illustrating an end tool of the surgical instrument of FIG. 1.
Figure 3:
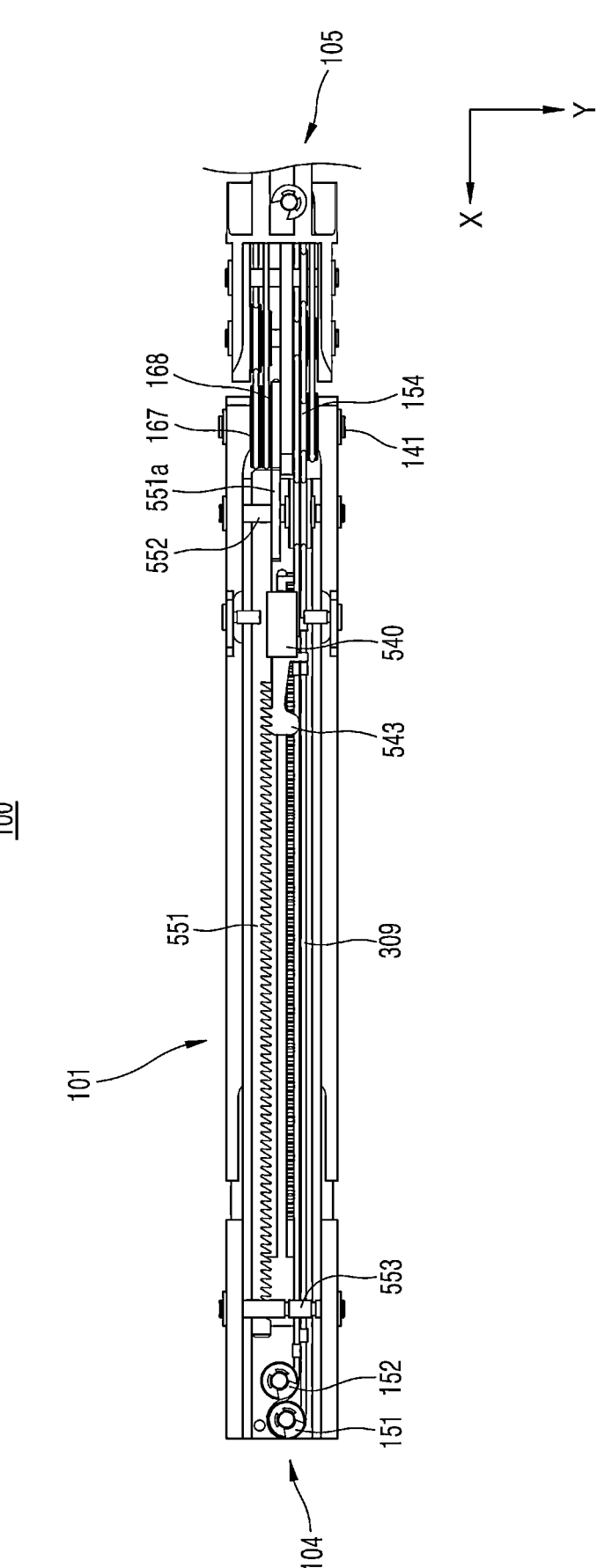
FIGS. 3 and 4 are plan views illustrating a first jaw of the end tool of the surgical instrument according to the first embodiment of the present disclosure.
Figure 4:
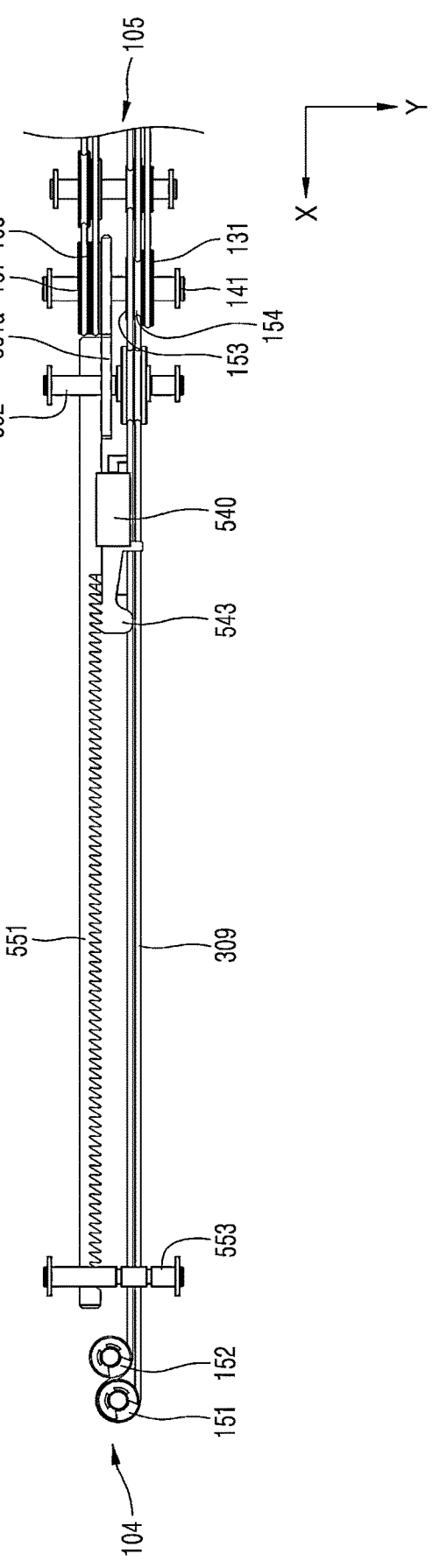
Figure 5:
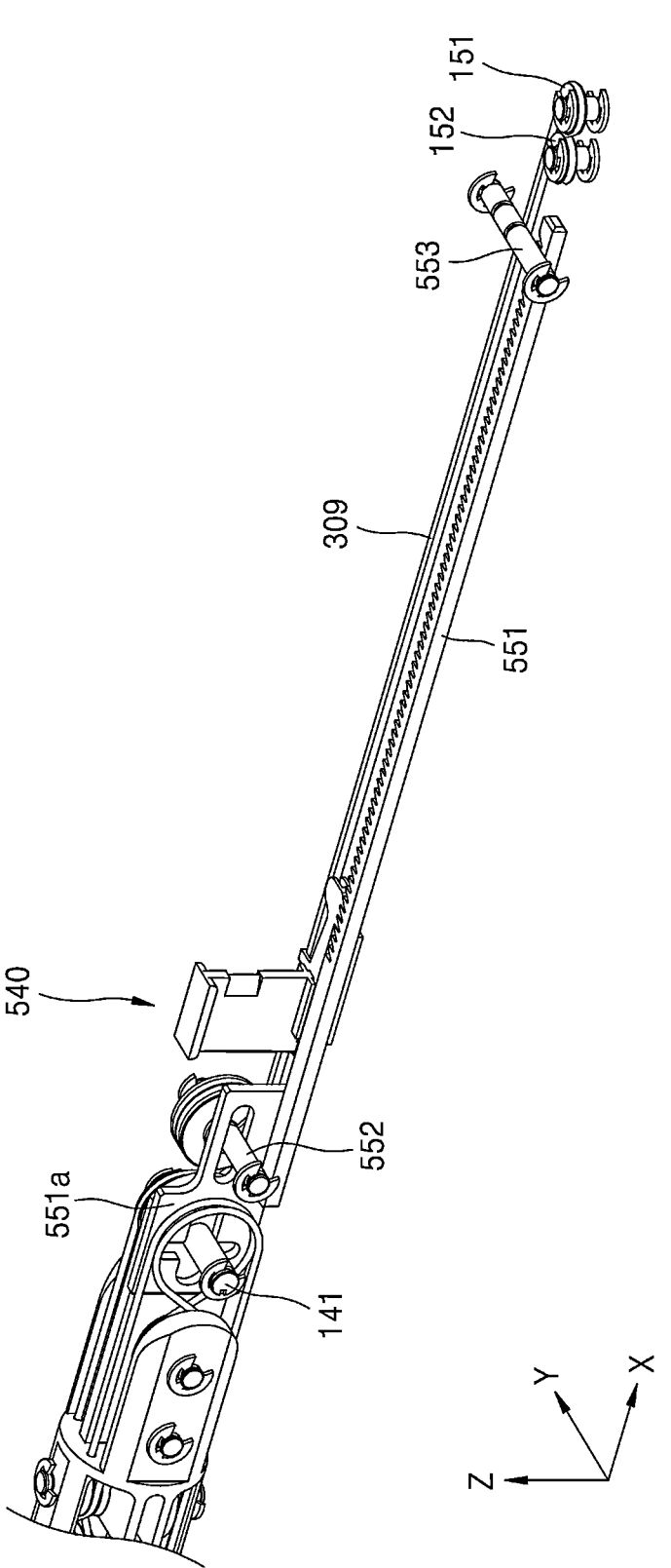
FIG. 5 is a perspective view illustrating the first jaw of the end tool of the surgical instrument according to the first embodiment of the present disclosure.

FIG. 1 is a perspective view illustrating a surgical instrument according to a first embodiment of the present disclosure, and FIG. 2 is a perspective view illustrating an end tool of the surgical instrument of FIG. 1. FIGS. 3 and 4 are plan views illustrating a first jaw of the end tool of the surgical instrument according to the first embodiment of the present disclosure, and FIG. 5 is a perspective view illustrating the first jaw of the end tool of the surgical instrument according to the first embodiment of the present disclosure.

First, referring to FIGS. 1 and 2, a surgical instrument 10 according to the first embodiment of the present disclosure includes an end tool 100, a manipulation part 200, a power transmission part (not shown) 300, and a connection part 400.

Here, the connection part 400 is formed in the shape of a hollow shaft, and one or more wires and electric wires may be accommodated therein. The manipulation part 200 is coupled to one end portion of the connection part 400, the end tool 100 is coupled to another end portion thereof, and the connection part 400 may serve to connect the manipulation part 200 to the end tool 100.

The manipulation part 200 is formed on one end portion of the connection part 400 and provided as an interface to be directly controlled by a medical doctor, for example, a tongs shape, a stick shape, a lever shape, or the like, and when the medical doctor controls the manipulation part 200, the end tool 100, which is connected to the interface and inserted into the body of a surgical patient, performs a certain motion, thereby performing surgery. Here, although the manipulation part 200 is illustrated in FIG. 1 as being formed in the form of a gripping part that can be wrapped with the palm and a lever that can be pulled with a finger, the concept of the present disclosure is not limited thereto, and various types of manipulation parts that are connected to the end tool 100 and manipulate the end tool 100 may be possible.

The end tool 100 is formed on another end portion of the connection part 400, and performs necessary motions for surgery by being inserted into a surgical site. In an example of the end tool 100, as illustrated in FIG. 1, a pair of jaws 103 for performing a grip motion may be used. However, the concept of the present disclosure is not limited thereto, and various devices for performing surgery may be used as the end tool 100. For example, a configuration such as a cantilever cautery may also be used as the end tool. The end tool 100 is connected to the manipulation part 200 by the power transmission part 300, and receives a driving force of the manipulation part 200 through the power transmission part 300 to perform a motion necessary for surgery, such as gripping, cutting, suturing, or the like.

Here, the end tool 100 of the surgical instrument 10 according to the first embodiment of the present disclosure is formed to be rotatable in at least one direction, for example, the end tool 100 may perform a pitch motion around a Y-axis of FIG. 1 and simultaneously perform a yaw motion and an actuation motion around a Z-axis of FIG. 1.

Here, each of the pitch, yaw, and actuation motions used in the present disclosure are defined as follows.

First, the pitch motion means a motion of the end tool 100 rotating in a vertical direction with respect to an extension direction of the connection part 400 (an X-axis direction of FIG. 1), that is, a motion rotating around the Y-axis of FIG. 1. In other words, the pitch motion means a motion of the end tool 100, which is formed to extend from the connection part 400 in the extension direction of the connection part 400 (the X-axis direction of FIG. 1), rotating vertically around the Y-axis with respect to the connection part 400.

Next, the yaw motion means a motion of the end tool 100 rotating in left and right directions, that is, a motion rotating around the Z-axis of FIG. 1, with respect to the extension direction of the connection part 400 (the X-axis direction of FIG. 1). In other words, the yaw motion means a motion of the end tool 100, which extends from the connection part 400 in the extension direction of the connection part 400 (the X-axis direction of FIG. 1), rotating horizontally around the Z-axis with respect to the connection part 400. That is, the yaw motion means a motion of the two jaws 103, which are formed on the end tool 100, rotating around the Z-axis in the same direction.

Meanwhile, the actuation motion means a motion of the end tool 100 rotating around the same shaft of rotation as that of the yaw motion, while the two jaws 103 rotate in opposite directions so as to be closed or opened. That is, the actuation motion means a motion of the two jaws 103, which are formed on the end tool 100, rotating in the opposite directions around the Z-axis.

The power transmission part 300 may serve to connect the manipulation part 200 to the end tool 100 to transmit the driving force of the manipulation part 200 to the end tool 100, and may include a plurality of wires, pulleys, links, sections, gears, and the like.

(Power Transmission Part)

Hereinafter, the power transmission part 300 of the surgical instrument 10 of FIG. 1 will be described in detail.

Referring to FIGS. 1 to 6 and the like, the power transmission part 300 of the surgical instrument 10 according to an embodiment of the present disclosure may include a plurality of wires including staple wires 307 and 308 and a backward-moving wire 309.

Here, two wires may be paired to serve as a first jaw wire or a second jaw wire, and may also serve as the staple wire or the backward-moving wire. The staple wire and the backward-moving wire will be described in detail later.

In addition, the power transmission part 300 of the surgical instrument 10 according to an embodiment of the present disclosure may include a coupling member (not shown) coupled to an end portion of each of the wires in order to couple the wires to the pulleys. Here, each of the coupling members may have various shapes as necessary, such as a ball shape, a tube shape, and the like.

As described above, each of the first jaw wire, the second jaw wire, the staple wire, and the backward-moving wire is formed of two separate wires, and the two wires may be connected to each other by the coupling member. Alternatively, the coupling member may be inserted at an intermediate point of one single wire, and crimped and fixed, and then, two strands of the single wire centered on the coupling member may be distinguished from each other.

The coupling member may then be coupled to the pulley, so that the wire may be fixedly coupled to the pulley. Accordingly, the pulley may be rotated as the wire is pulled and released.

Meanwhile, at the manipulation part 200 side, a first jaw wire-manipulation part coupling member may be coupled to an end portion of the wire, which is opposite to the end portion of the wire at the end tool 100 side to which the coupling member is coupled.

In addition, as the first jaw wire-manipulation part coupling member is coupled to a pulley of the manipulation part 200, the wire may be fixedly coupled to the pulley of the manipulation part 200. As a result, when the pulley of the manipulation part 200 is rotated by a motor or human force, a pulley of the end tool 100 may be rotated as the wire is pulled and released.

In the same manner, the second jaw wire may connect a jaw pulley of the end tool 100 to a pulley (not shown) of the manipulation part 200, and the staple wires 307 and 308 may connect staple pulleys 167 and 168 of the end tool 100 to pulleys (not shown) of the manipulation part 200. In addition, the backward-moving wire 309 may connect a backward-moving wire pulley 151 of the end tool 100 to a pulley (not shown) of the manipulation part 200.

(End Tool)

Hereinafter, the end tool 100 of the surgical instrument 10 of FIG. 1 will be described in detail.

Referring to FIGS. 1 and 2, the end tool 100 of the first embodiment of the present disclosure includes a pair of jaws for performing a grip motion, that is, a first jaw 101 and a second jaw 102. Here, each of the first jaw 101 and the second jaw 102, or a component encompassing the first jaw 101 and the second jaw 102 may be referred to as the jaw 103.

In addition, the end tool 100 may include a cartridge 500, a staple drive assembly 150, the backward-moving wire 309, and any other structure associated with backward-movement driving, which will be described later.

In addition, the end tool 100 may include an end tool hub 180. The end tool hub 180 has one end portion through which a jaw rotation shaft 141 is inserted, and may be axially coupled to the first jaw 101 by the jaw rotation shaft 141.

A pulley 131 serving as a pitch pulley, the staple pulleys 167 and 168 to be described later, a reciprocating member 551, loop pulleys 153 and 154, and the like may be axially coupled to the rotation shaft 141 to be partially accommodated in the first jaw 101.

Here, the pulleys facing each other are illustrated in the drawings as being formed parallel to each other, but the concept of the present disclosure is not limited thereto, and each of the pulleys may be variously formed with a position and a size suitable for the configuration of the end tool.

(Staple Drive Components)

Figure 6:
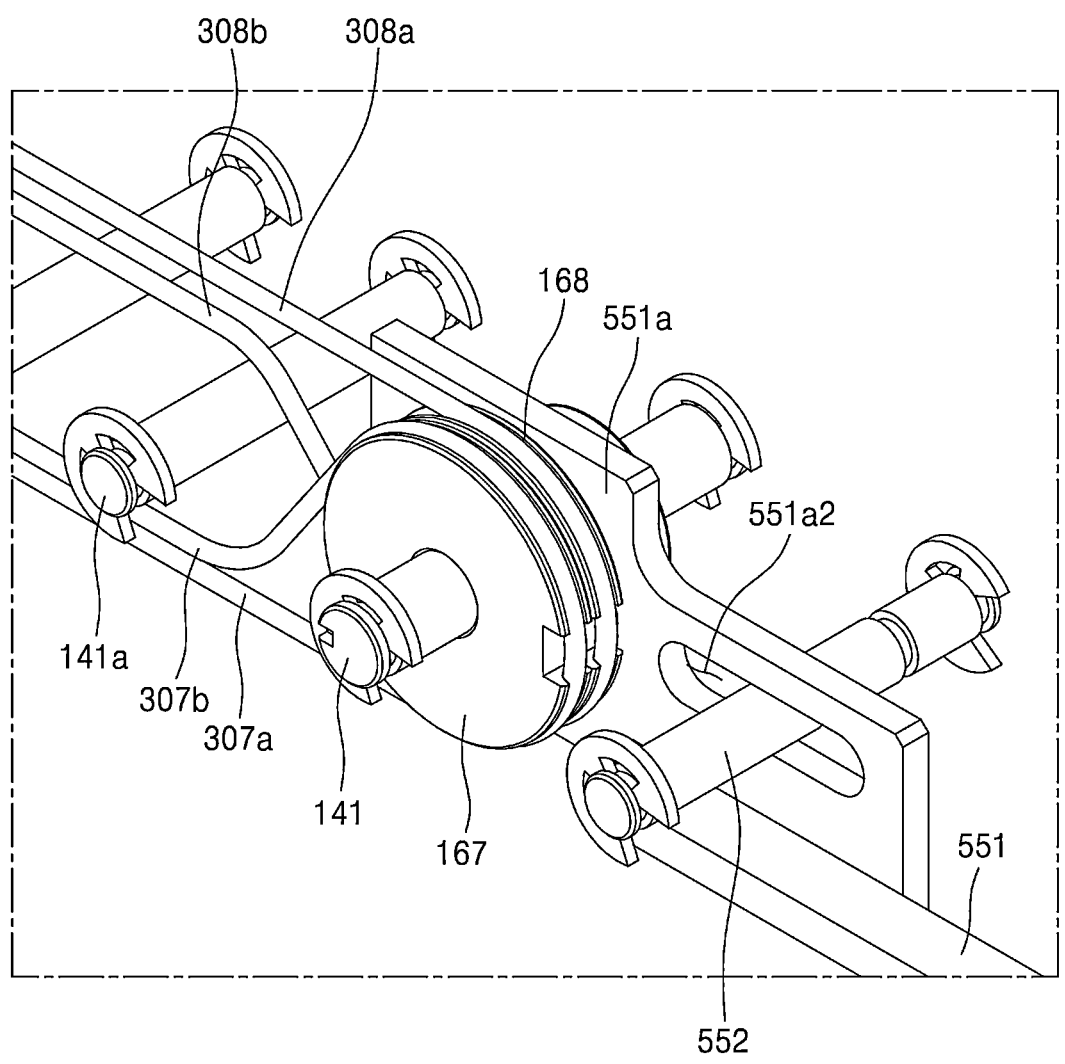
FIGS. 6 and 7 are perspective views illustrating a slot part of a reciprocating member and staple pulleys of FIG. 3.
Figure 7:
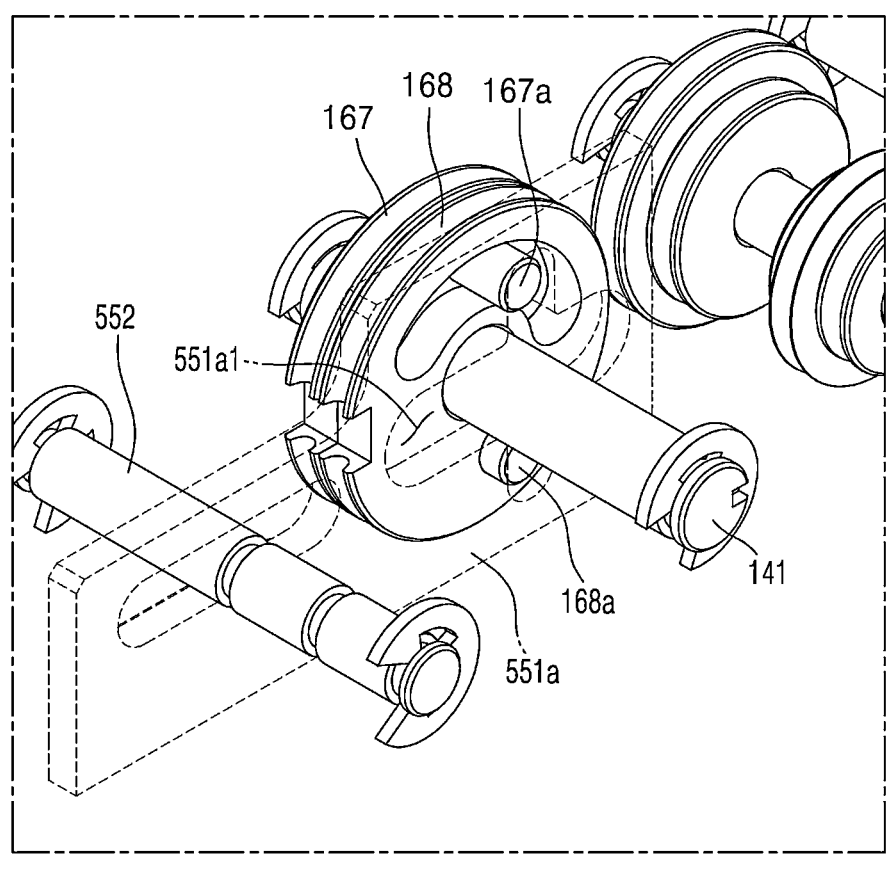
Figure 8:
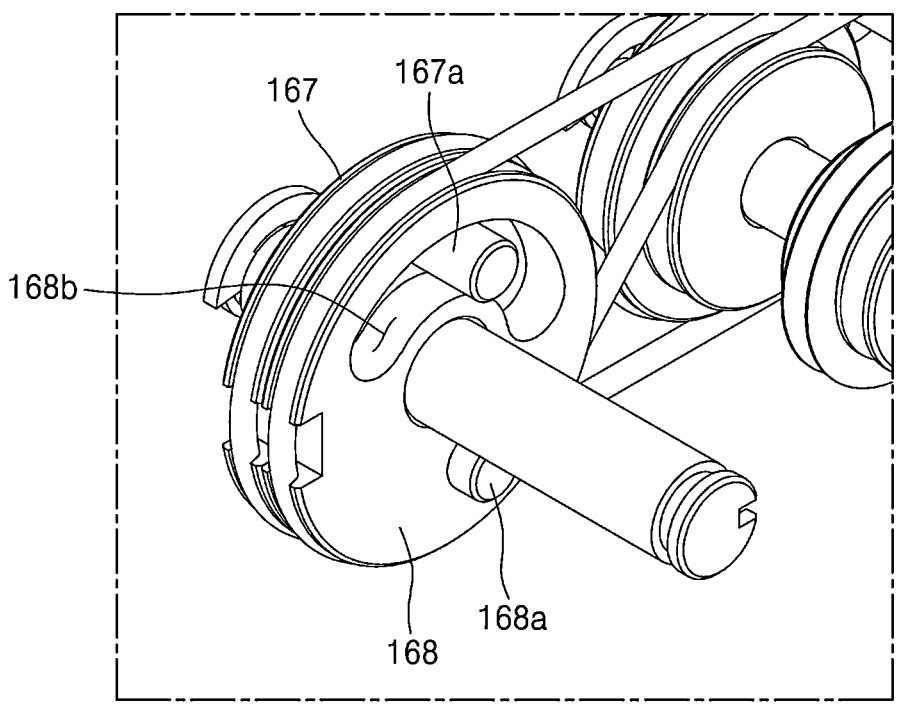
FIG. 8 is a perspective view illustrating the staple pulleys of FIG. 3.

FIGS. 6 and 7 are perspective views illustrating a slot part of the reciprocating member and the staple pulleys of FIG. 3, and FIG. 8 is a perspective view illustrating the staple pulleys of FIG. 3.

Referring to FIGS. 6 to 8 and the like, the first jaw 101 of the end tool 100 of the surgical instrument according to the first embodiment of the present disclosure may include a reciprocating assembly 550, an operation member 540, the staple drive assembly 150, the jaw rotation shaft 141, the staple pulleys 167 and 168, the backward-moving wire 309, the backward-moving wire pulley 151, the loop pulleys 153 and 154, and the like.

First, the staple drive assembly 150 and the reciprocating assembly 550 will be described in detail in connection with a stapling motion.

The staple drive assembly 150 of the present embodiment may include two staple pulleys 167 and 168. Here, the staple drive assembly 150 is connected to the reciprocating assembly 550 to be described later, and converts a rotational motion of the staple pulleys 167 and 168 into a linear motion of the reciprocating assembly 550.

Referring to FIGS. 6 to 8 again, the staple pulley 167 and the staple pulley 168 may be configured as a single set. In an example, the staple pulley 167 and the staple pulley 168 may be disposed on both sides of the reciprocating member 551 with the reciprocating member 551 interposed therebetween or may be disposed on any one side surface of the reciprocating member 551. Each of the staple pulley 167 and the staple pulley 168 may have a through hole formed at the center thereof, and the rotation shaft 141 may be inserted therethrough. As shown in the drawings, when both the staple pulley 167 and the staple pulley 168 are disposed on one side surface of a slot part 551a of the reciprocating member 551, the staple pulleys 167 and 168 may have a pin/slot structure in order for both the staple pulley 167 and the staple pulley 168 to be connected to the reciprocating member 551. That is, a mechanism for transferring a rotational motion of the staple pulleys 167 and 168 as a linear motion of the reciprocating member 551 is required, and this mechanism will be described in detail below.

Specifically, when referring to the pulley that is more adjacent to the side of the reciprocating member 551 among the staple pulleys as the staple pulley 168 at the inner side surface, and referring to another pulley as the staple pulley 167 at the outer side surface, a pulley pin 168a protruding toward the slot part 551a of the reciprocating member 551, which will be described later, may be formed in the staple pulley 168 at the inner side surface. The pulley pin 168a may be formed on an inner side surface of the staple pulley 168 so as to be adjacent to or spaced apart from the rotation shaft 141 that is inserted through the staple pulley 168. in addition, the pulley pin 168a may be inserted into a slot 551a1 of the reciprocating member 551.

In addition, a slot 168b may be formed in the staple pulley 168 at a side opposite to the side in which the pulley pin 168a is formed with respect to the rotation shaft 141. The slot 168b of the staple pulley 168 may be one region through which a pulley pin 167a of the staple pulley 167 to be described later is inserted.

The pulley pin 167a protruding toward the slot part 551a of the reciprocating member may be formed on the staple pulley 167 at the outer side surface, and the pulley pin 167a may be inserted into the slot 551a1 of the reciprocating member through the staple pulley 168 at the inner side surface. In other words, the pulley pin 167a of the staple pulley 167 may be inserted into the slot 551a1 of the reciprocating member through the slot 168b of the staple pulley 168.

Since the pulley pin 167a is rotated around the rotation shaft 141 as the staple pulley 167 rotates around the rotation shaft 141, to prevent interference with the staple pulley 168, the slot 168b of the staple pulley 168 may be formed with a clearance space to allow the pulley pin 167a to move freely.

Meanwhile, in a state in which the pulley pin 167a of the staple pulley 167 is inserted into the slot 168b of the staple pulley 168, the pulley pin 167a may be formed on the opposite side to the pulley pin 168a of the staple pulley 168 with respect to the rotation shaft 141. In addition, the pulley pin 167a and the pulley pin 168a may serve to convert a rotational motion of the staple pulleys 167 and 168 into a linear motion of the reciprocating member by being connected to the slot part 551a of the reciprocating member to be described later.

Hereinafter, the linear motion of the reciprocating member 551 in relation to the connection relationship between the reciprocating member 551 and the staple pulleys 167 and 168 will be described in detail.

The reciprocating member 551 is formed in the form of a bar elongated in a longitudinal direction of the first jaw 101, and the slot part 551a may be formed at a proximal end side of the reciprocating member 551, to which the staple pulleys 167 and 168 are connected.

The slot part 551a of the reciprocating member 551 may be formed as a plate-shaped member that may come into contact with the surface generated through the rotation of the staple pulleys 167 and 168, and may be formed as a member independent of the reciprocating member 551 having a bar shape or may be formed integrally with the reciprocating member 551. In addition, the slot 551a1 through which the rotation shaft 141, the pulley pin 167a, and the pulley pin 168a pass may be formed in the slot part 551a.

Specifically, the slot 551a1 may be formed in a longitudinal direction of the reciprocating member 551, enabling linear movement of the slot part 551a relative to the rotation shaft 141 while the rotation shaft 141 is inserted into the slot 551al. In other words, the slot 551al may be formed such that the reciprocating member 551 may linearly move away from or close to the rotation shaft 141.

Further, the slot 551a1 may be obtained by integrally forming a region of the slot 551al through which the pulley pin 167a and the pulley pin 168a pass and a slot region into which the rotation shaft 141 is inserted. In addition, a slot 551a2 independent of the slot 551al through which the rotation shaft 141, the pulley pin 167a, and the pulley pin 168a pass may be formed in the slot part 551a. The slot 551a2 is a region into which a longitudinal member 552 to be described later is inserted, and may be formed in a longitudinal direction, which is parallel to a linear motion direction of the reciprocating member 551, similar to the slot 551al.

Meanwhile, since the rotation shaft 141 and the longitudinal member 552 are fixedly positioned to the first jaw 101 and the slot part 551a is not directly fixed to the first jaw 101, the slot part 551a may move in response to the rotation of the staple pulleys 167 and 168. That is, the reciprocating member 551 coupled to the slot part 551a may move.

As the slot 551al and the slot 551a2 are formed in the longitudinal direction of the first jaw 101, that is, in the longitudinal direction corresponding to the longitudinal direction of the reciprocating member 551 as described above, the reciprocating member 551 may move only in the longitudinal direction of the first jaw 101.

Meanwhile, referring to FIG. 6 again, the staple wire connected to the staple pulley 167 may be formed by coupling a wire 307a to a wire 307b by a coupling member (not shown) or may be formed as a single wire. Here, for convenience, the staple wire will be described by dividing the staple wire into the wire 307a and the wire 307b.

Likewise, the staple wire connected to the staple pulley 168 may be formed by coupling a wire 308a to a wire 308b by a coupling member (not shown) or may be formed as a single wire. Here, for convenience, the staple wire will be described by dividing the staple wire into the wire 308a and the wire 308b.

As the staple wire is pulled and released, the staple pulley is rotationally moved. That is, referring to FIG. 6, as the wire 307a is pulled toward a proximal end of the end tool and the wire 307b is released toward a distal end of the end tool based on a direction shown in the drawing (i.e., a direction in which a distal end of a first jaw faces the right side), the staple pulley 167 is rotated in a clockwise direction, and in the opposite case, the staple pulley 167 is rotated in a counterclockwise direction. Further, as the wire 308b is pulled toward the proximal end of the end tool and the wire 308a is released toward the distal end, the staple pulley 168 is rotated in the clockwise direction, and in the opposite case, the staple pulley 168 is rotated in the counterclockwise direction.

Describing with reference to FIG. 7 again, since the pulley pin 167a of the staple pulley 167 and the pulley pin 168a of the staple pulley 168 are coupled to the slot part 551a of the reciprocating member 551, the slot part 551a may operate as follows in response to the rotation the staple pulleys 167 and 168.

As the staple pulley 168 rotates in the clockwise direction with respect to the direction shown in the drawing (i.e., the direction in which the distal end of the first jaw faces the left side), the pulley pin 168a positioned below the rotation shaft 141 may push the slot 551al of the slot part 551a toward the distal end of the end tool, and as the staple pulley 167 rotates in the counterclockwise direction, the pulley pin 167a positioned above the rotation shaft 141 may push the slot 551al of the slot part 551a toward the distal end of the end tool On the contrary, as the staple pulley 168 rotates in the counterclockwise direction, the pulley pin 168a positioned below the rotation shaft 141 may pull the slot 551al of the slot part 551a toward the proximal end of the end tool, and as the staple pulley 167 rotates in the clockwise direction, the pulley pin 167a positioned above the rotation shaft 141 may pull the slot 551al of the slot part 551a toward the proximal end of the end tool.

Meanwhile, the staple pulley 167 and the staple pulley 168 always rotate in opposite directions, so that rotational forces transmitted to the first jaw 101 may be canceled out by the staple wires 307 and 308.

Specifically, referring to FIGS. 6 and 7 again, as viewed from the direction in which the distal end of the first jaw 101 faces the right side, when the wire 308a is pulled, the staple pulley 168 is rotated in the counterclockwise direction, and the reciprocating member 551 is moved toward the distal end of the end tool. At this time, a force by which the wire 308a rotates the staple pulley 168 in the counterclockwise direction may act as a force to cause the reciprocating member 551 and the first jaw 101 to rotate in the counterclockwise direction relative to the rotation shaft 141.

On the other hand, when the wire 307a is pulled, the staple pulley 167 is rotated in the clockwise direction, and the reciprocating member 551 is moved toward the proximal end of the end tool. At this time, a force by which the wire 307a rotates the staple pulley 167 in the clockwise direction may act as a force to cause the reciprocating member 551 and the first jaw 101 to rotate in the clockwise direction relative to the rotation shaft 141.

Since the staple pulleys 167 and 168 rotate in opposite directions as described above, the rotational forces transmitted to the first jaw 101 through the staple wires 307 and 308 may be canceled out. In other words, in order to linearly move the reciprocating member 551 in the same direction, the staple pulley 167 and staple pulley 168 always rotate in opposite directions either in the clockwise-counterclockwise directions or the counterclockwise-clockwise directions, so that rotational forces transmitted to the first jaw 101 through the staple wires 307 and 308 can be canceled out.

Meanwhile, the end tool 100 according to the embodiment of the present disclosure may further include a longitudinal member 553 formed at the distal end side of the end tool.

The longitudinal member 553 may serve to support the reciprocating member 551 together with the longitudinal member 552 described above. In other words, it may be described that a device capable of restricting a vertical movement (in a Z-axis direction) of the reciprocating member 551 is provided, ensuring that the rotation of the staple pulleys 167 and 168 results only in linear movement of the reciprocating member 551. Specifically, the longitudinal member 553 may function as a member that does not interfere with the linear motion of the reciprocating member 551 in the longitudinal direction of the first jaw 101 and resist the end portion of the reciprocating member 551 at the distal end side from rising.

(Cartridge)

Hereinafter, the cartridge 500 of the surgical instrument 10 of FIG. 1 will be described in more detail.

Figure 9:
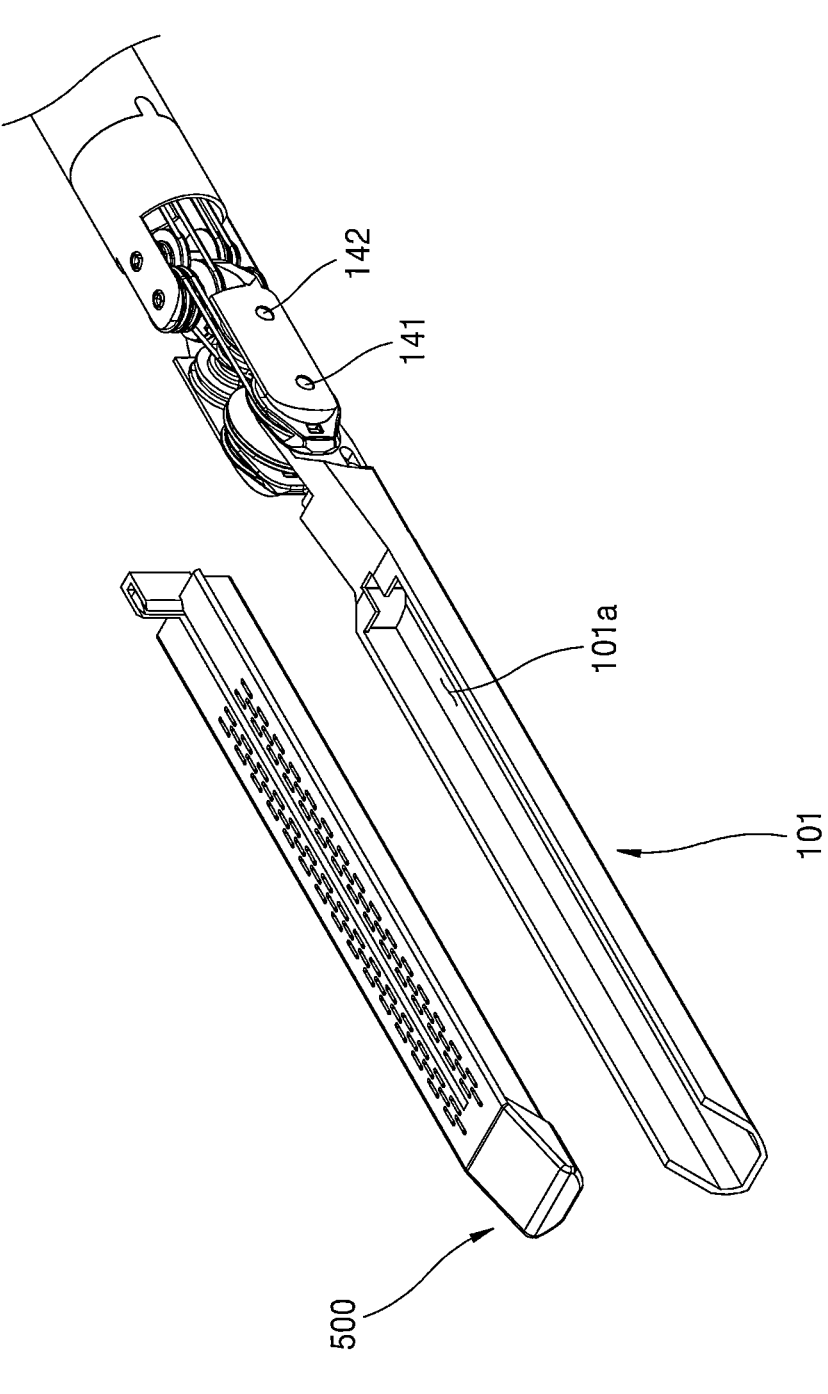
FIG. 9 is a perspective view illustrating the first jaw and a cartridge of the surgical instrument of FIG. 1.
Figure 10:
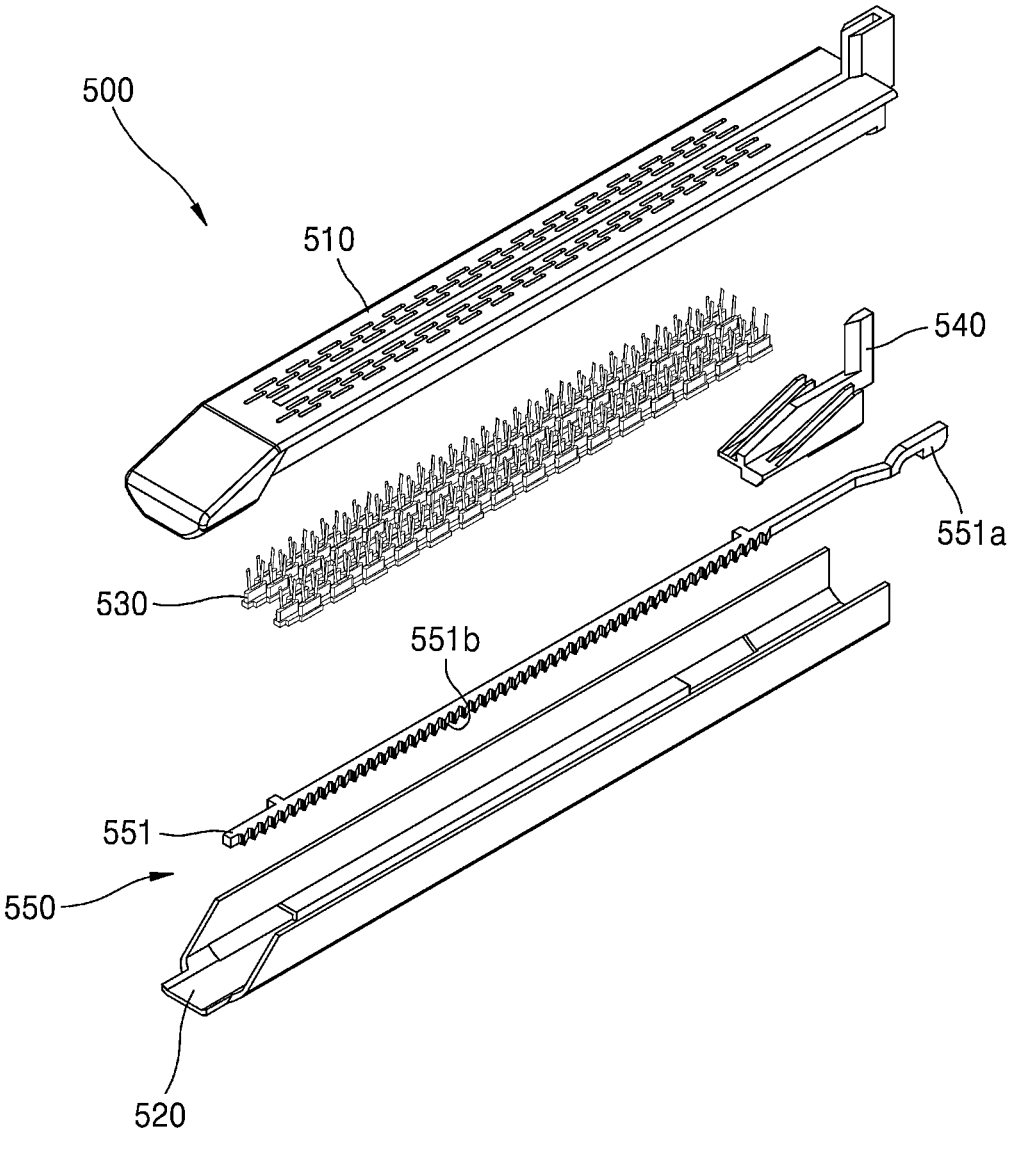
FIG. 10 is an exploded perspective view illustrating the cartridge of FIG. 9.
Figure 11:
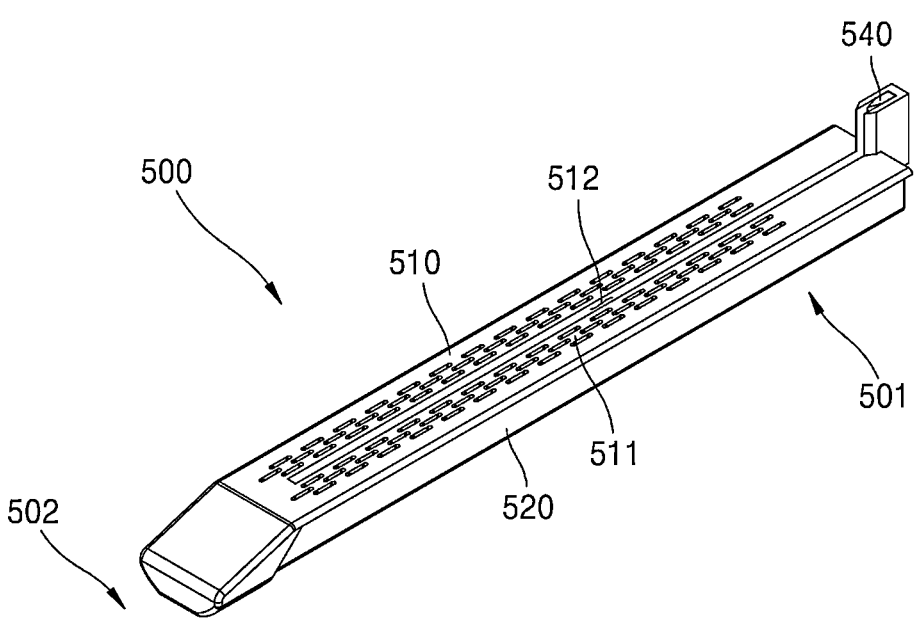
FIG. 11 is an assembled perspective view illustrating the cartridge of FIG. 9.
Figure 12:
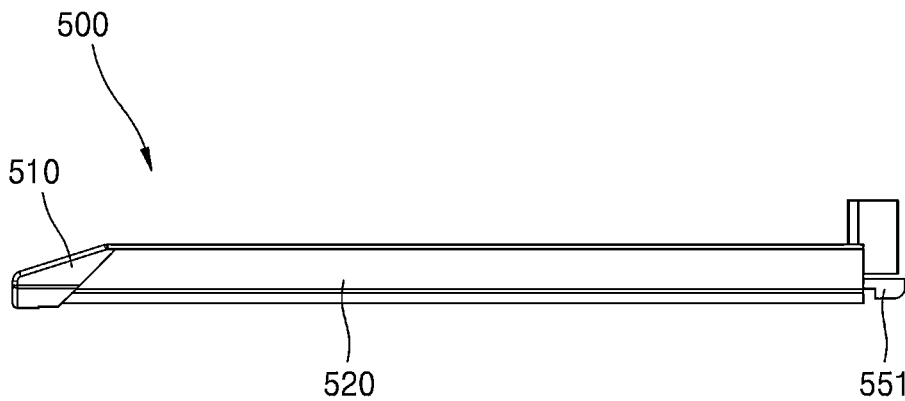
FIG. 12 is a side view illustrating the cartridge of FIG. 9.
Figure 13:
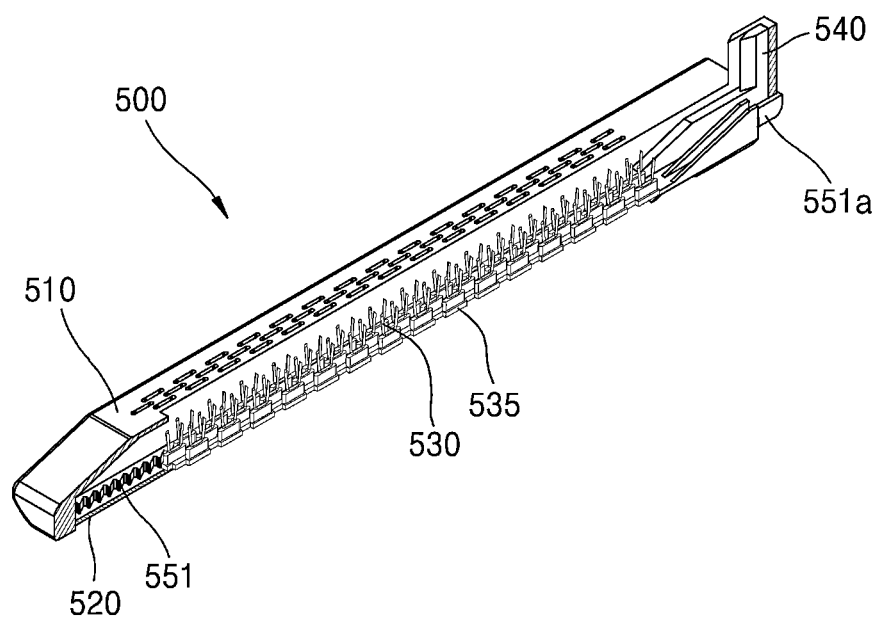
FIG. 13 is a perspective cross-sectional view illustrating the cartridge of FIG. 9.
Figure 14:
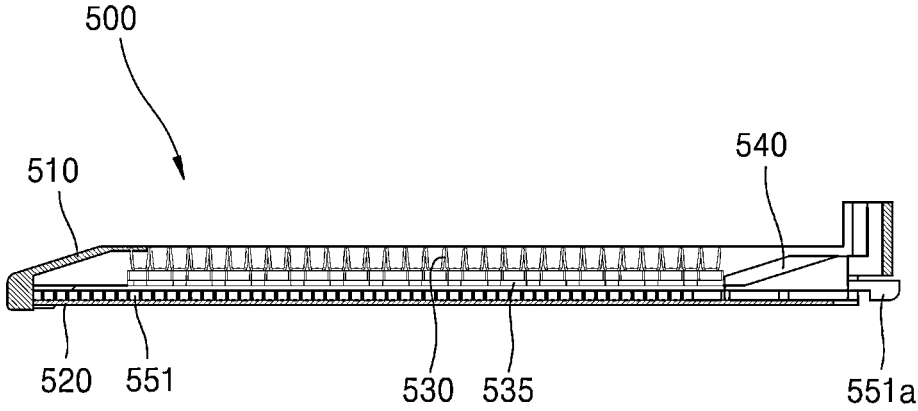
FIG. 14 is a side cross-sectional view illustrating the cartridge of FIG. 9.
Figure 15:
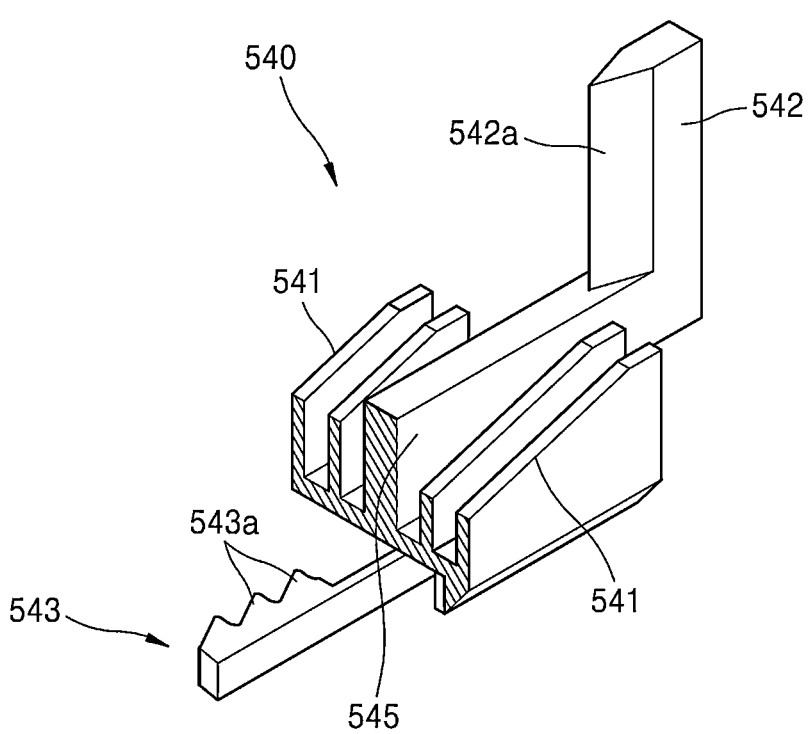
FIGS. 15 and 16 are perspective views illustrating an operation member of the cartridge of FIG. 9.
Figure 16:
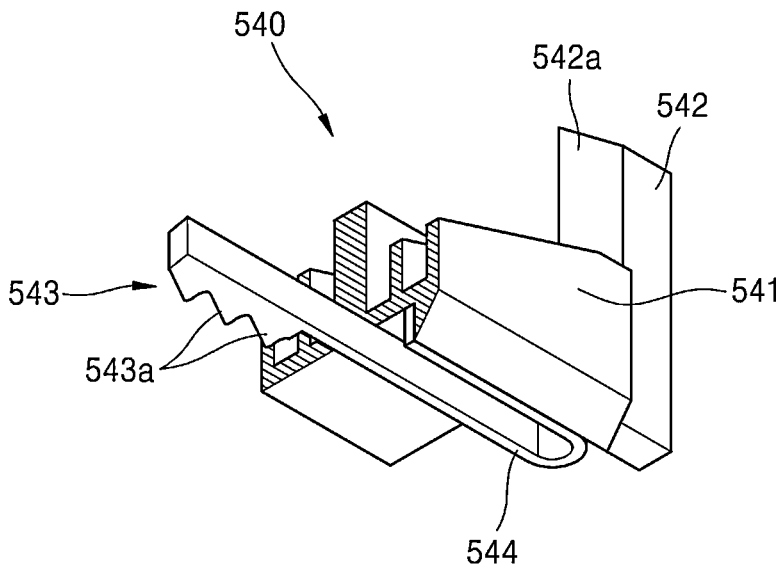
Figure 17:
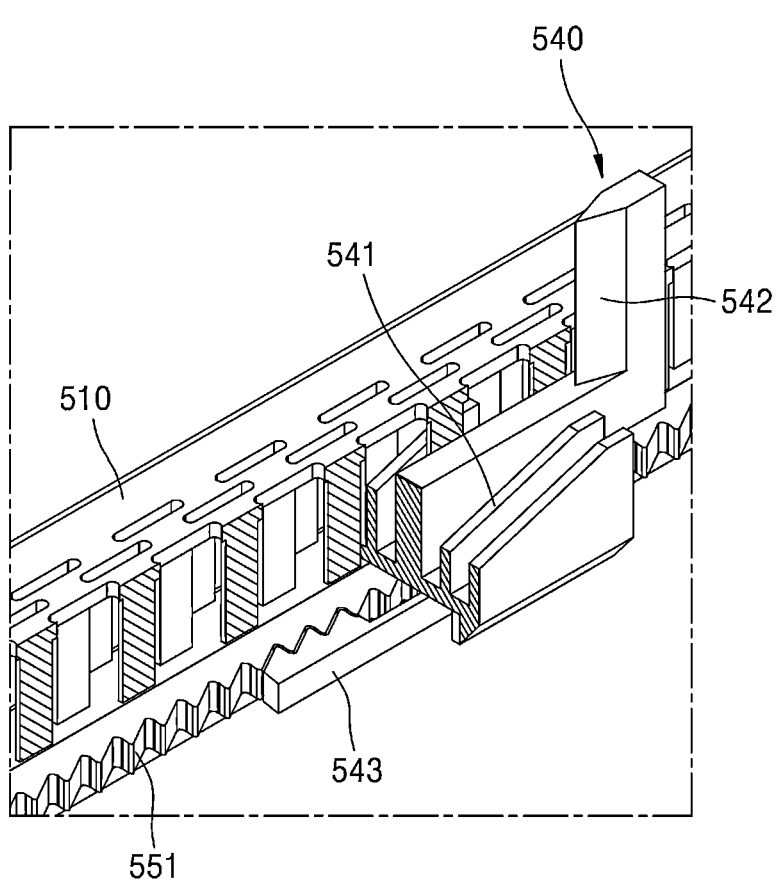
FIGS. 17 to 20 are perspective views illustrating a ratchet drive operation of the end tool of FIG. 1.
Figure 18:
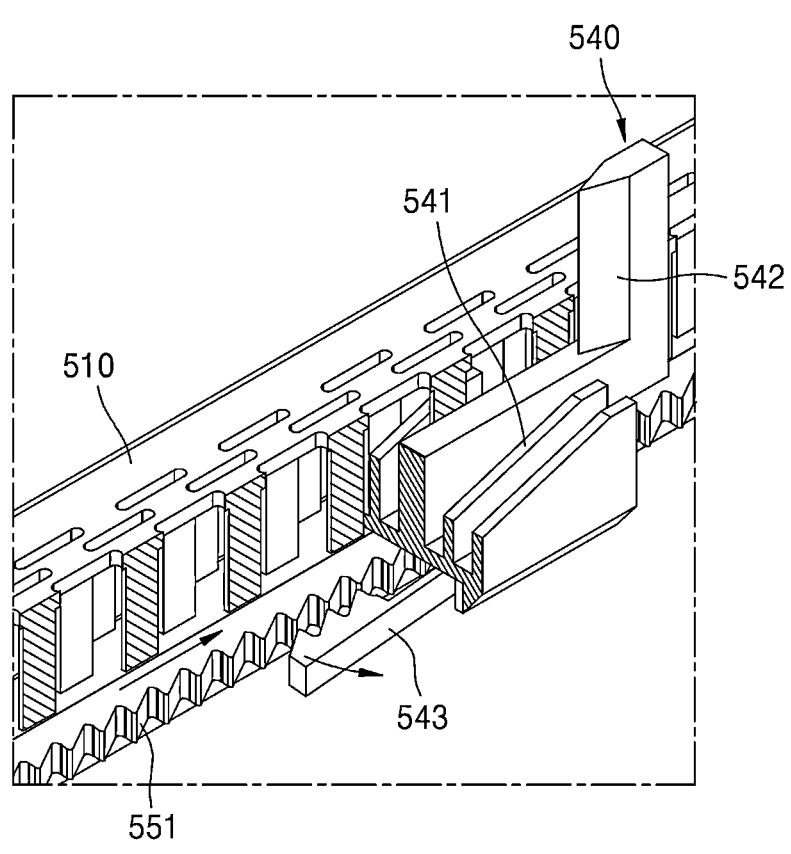
Figure 21:
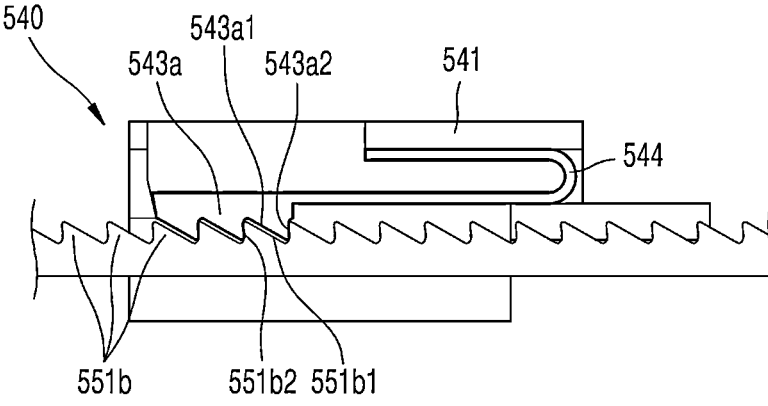
FIGS. 21 and 22 are plan views illustrating a ratchet drive operation of the end tool of FIG. 1.
Figure 22:
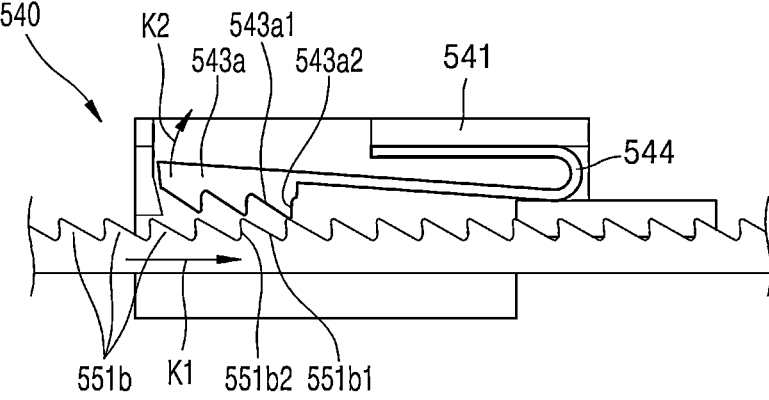
Figure 23A:
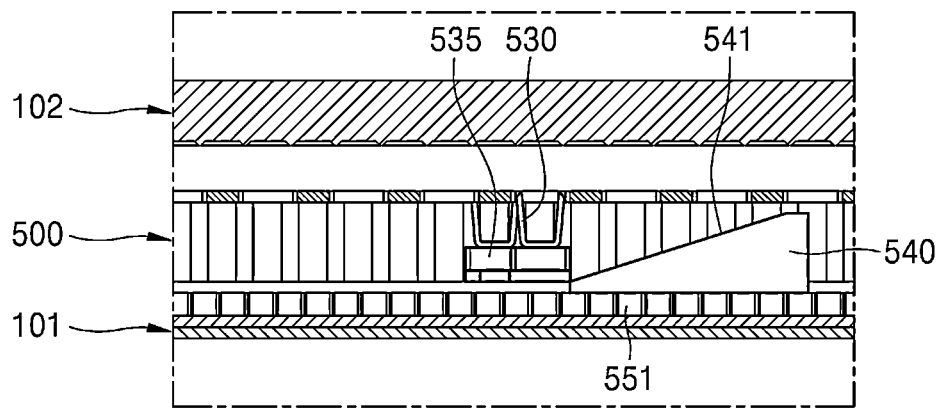
FIGS. 23A, 23B, and 23C are side cross-sectional views illustrating an entire stapling motion of the end tool of FIG. 1.
Figure 23B:
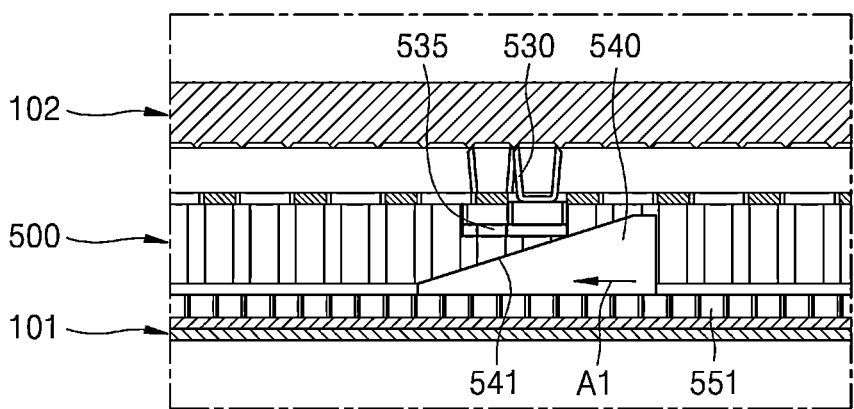
Figure 23C:
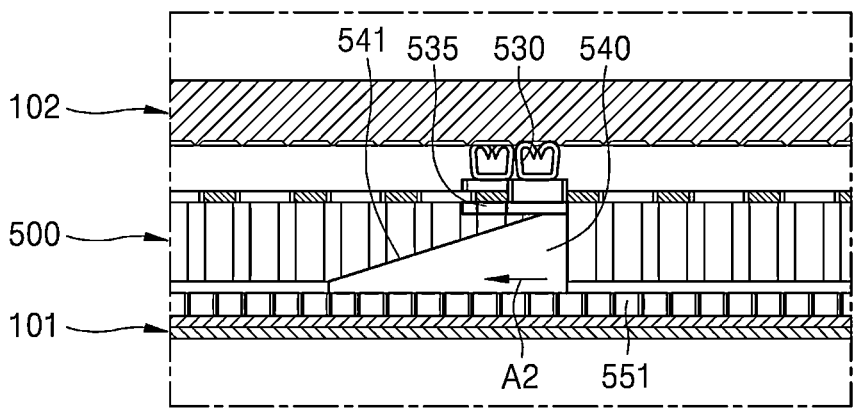

FIG. 9 is a perspective view illustrating the first jaw and the cartridge of the surgical instrument of FIG. 1. FIG. 10 is an exploded perspective view illustrating the cartridge of FIG. 9, FIG. 11 is an assembled perspective view illustrating the cartridge of FIG. 9, and FIG. 12 is a side view illustrating the cartridge of FIG. 9. FIG. 13 is a perspective cross-sectional view illustrating the cartridge of FIG. 9, and FIG. 14 is a side cross-sectional view illustrating the cartridge of FIG. 9. FIGS. 15 and 16 are perspective views illustrating the operation member of the cartridge of FIG. 9. FIGS. 17 to 20 are perspective views illustrating a ratchet drive operation of the end tool of FIG. 1, and FIGS. 21 and 22 are plan views illustrating a ratchet drive operation of the end tool of FIG. 1. FIGS. 23A to 23C are side cross-sectional views illustrating an entire stapling motion of the end tool of FIG. 1.

Referring to FIGS. 9 to 23C and the like, the cartridge 500 is formed to be mountable to and dismountable from the first jaw 101, and includes a plurality of staples 530 and a blade 542 therein to perform suturing and cutting tissue. Here, the cartridge 500 may include a cover 510, a housing 520, the staples 530, withdrawal members 535, the operation member 540, and the reciprocating assembly 550.

The housing 520 forms an outer shape of the cartridge 500, and may be formed entirely in the form of a hollow box with one surface (upper surface) thereof is removed to accommodate the reciprocating assembly 550, the operation member 540, and the staples 530 therein. Here, the housing 520 may be formed in an approximately "U" shape in cross section.

The cover 510 is formed to cover an upper portion of the housing 520. Staple holes 511 through which the plurality of staples 530 may be ejected to the outside may be formed in the cover 510. As the staples 530, which are accommodated inside the housing 520 before a stapling operation, are pushed and raised upward by the operation member 540 during a stapling motion, and pass through the staple holes 511 of the cover 510 to be withdrawn to the outside of the cartridge 500, stapling is performed.

Meanwhile, a slit 512 may be formed in the cover 510 along a longitudinal direction of the cover 510. The blade 542 of the operation member 540 may protrude out of the cartridge 500 through the slit 512. As the blade 542 of the operation member 540 passes along the slit 512, staple-completed tissue may be cut.

The plurality of staples 530 may be disposed inside the housing 520. As the operation member 540, which will be described later, is linearly moved in one direction, the plurality of staples 530 are sequentially pushed and raised from the inside of the housing 520 to the outside, thereby performing suturing, that is, stapling. Here, the staples 530 may be made of a material that may include titanium, stainless steel, or the like.

Meanwhile, the withdrawal member 535 may be further disposed between the housing 520 and the staple 530. In other words, it may be said that the staple 530 is disposed above the withdrawal member 535. In this case, the operation member 540 is linearly moved in one direction to push and raise the withdrawal member 535, and the withdrawal member 535 may push and raise the staple 530.

As such, the operation member 540 may be described as pushing and raising the staples 530 in both the case in which the operation member 540 directly pushes and raises the staples 530 and the case in which the operation member 540 pushes and raises the withdrawal members 535 and the withdrawal members 535 pushes and raises the staples 530 (i.e., the operation member 540 indirectly pushes and raises the staples 530).

The reciprocating assembly 550 may be disposed at an inner lower side of the housing 520. Alternatively, the reciprocating assembly 550 may be disposed between the housing 520 and the first jaw 101. The reciprocating assembly 550 may include one or more reciprocating members 551. In the present embodiment, it is illustrated that one reciprocating member 551 is provided, but a plurality of reciprocating members 551 may be provided.

In the present embodiment, the reciprocating member 551 may be a rack. The reciprocating member 551 may include recesses 551*b* and the slot part 551*a*. In detail, the reciprocating member 551 may be formed in the form of an elongated bar, and a plurality of recesses 551*b* having a sawtooth shape may be formed on one surface thereof. The recess 551*b* may be formed to be in contact with the operation member 540 to be described later, in particular, a ratchet member 543 of the operation member 540. In other words, the reciprocating member 551 may include the plurality of recesses 551*b* shaped to engage with ratchets 543*a* of the ratchet member 543.

Meanwhile, although not shown in the drawings, in addition to a rack shape, the reciprocating member 551 may be provided as various shapes of members, which are directly or indirectly connected to the staple pulleys 167 and 168, and may perform a linear reciprocating motion according to a rotational motion of the staple pulleys 167 and 168. For example, the reciprocating member 551 may be in the form of a clutch in which recesses are not present.

Here, the reciprocating member 551 is not fixedly coupled to the other components of the cartridge 500, and may be formed to be movable relative to the other components of the cartridge 500. That is, the reciprocating member 551 may perform a reciprocating linear motion with respect to the housing 520 and the cover 510 coupled to the housing 520.

Meanwhile, in the reciprocating member 551, the slot part 551*a* may be formed at a proximal end 501 side adjacent to the rotation shaft 141, and the rotation shaft 141 of the end tool 100 may be inserted through and coupled to the slot part 551*a*. Thus, when the slot part 551*a* performs a reciprocating linear motion in the extension direction of the connection part 400 (i.e., in the X-axis direction), the reciprocating member 551 coupled thereto may also perform a reciprocating linear motion in the extension direction of the connection part 400 (i.e., in the X-axis direction). This will be described in more detail later.

The operation member 540 may be disposed inside the housing 520. The operation member 540 is formed to be in contact with the reciprocating member 551, and may be formed to linearly move in one direction according to the reciprocating linear motion of the reciprocating member 551. In other words, the operation member 540 interacts with the reciprocating member 551 to perform stapling and cutting motions while moving in the extension direction of the connection part 400.

The operation member 540 may include a wedge 541, the blade 542, the ratchet member 543, an elastic member 544, and a body 545.

The body 545 may be formed in the shape of an elongated square column, and forms a base of the operation member 540.

The wedge 541 is formed on at least one side of the body 545, and may be formed to have a predetermined inclined surface. That is, the wedge 541 may be formed to be inclined to a certain extent in the extension direction of the connection part 400. In other words, the wedge 541 may be formed to have a greater height at the proximal end 501 side of the cartridge 500 than a distal end 502 side of the cartridge 500. In the drawing, it is illustrated that two wedges 541 are formed on each side of the body 545 in the left and right direction, but the concept of the present disclosure is not limited thereto, and the wedge 541 may be formed in various numbers and shapes depending on the shape of the staple 530 or the withdrawal member 535 that is in contact with the wedge 541.

The wedge 541 may be formed to be in contact with the withdrawal members 535 or the plurality of staples 530 in turn and may serve to sequentially push and raise the staples 530. As shown in FIGS. 23A to 23C to be described later and elsewhere herein, the operation member 540 may serve to withdraw the staples 530 to the outside of the cartridge 500 by sequentially pushing and raising the staples 530 while moving toward the distal end 502.

The blade 542 may be formed at one side of the wedge 541, more specifically, at one side of the wedge 541 at the proximal end 501 side. An edge 542a formed to be sharp to cut tissue is formed in one region of the blade 542. As at least a portion of the edge 542a is withdrawn to the outside of the first jaw 101 and the cartridge 500, tissue disposed between the first jaw 101 and the second jaw 102 may be cut. The edge 542a of the blade 542 may be always withdrawn to the outside of the first jaw 101. Alternatively, the edge 542a of the blade 542 may normally be accommodated inside the first jaw 101 or inside the cartridge 500, and may be withdrawn to the outside of the first jaw 101 only when the operation member 540 is moved in a longitudinal direction.

The ratchet member 543 is formed on one side of the wedge 541, more specifically, below wedge 541, and may be formed to face the reciprocating member 551 to be described later. The ratchet member 543 may be formed in the form of a bar and may include a plurality of ratchets 543a on one surface. The operation member 540 is moved only in one direction (i.e., toward the distal end) with respect to the reciprocating member 551 by the ratchet member 543. The ratchets 543a of the ratchet member 543 may be formed to be in contact with the recess 551b of the reciprocating member 551 described above.

The elastic member 544 is formed on one side of the body 545 or the wedge 541 and serves to apply a predetermined elastic force to the ratchet member 543. In an example, one region of the elastic member 544 may be connected to the wedge 541 or the body 545, and another region of the elastic member 544 may be connected to the ratchet member 543, so that the elastic member 544 may connect the wedge 541 or the body 545 to the ratchet member 543. Here, the elastic member 544 may apply an elastic force in a direction in which the ratchet member 543 comes into close contact with the reciprocating member 551. To this end, the elastic member 544 may be formed in the form of a leaf spring, and may be provided in various forms capable of providing a predetermined elastic force to the ratchet member 543, such as a coil spring, a dish spring, and the like.

Here, the ratchet 543a of the ratchet member 543 may be formed such that a first surface 543a1 (specifically, at the distal end 502 side) is formed to have a gentle slope with a predetermined angle, and a second surface 543a2 (specifically, at the proximal end 501 side) is formed to be vertical or near vertical.

In addition, in order to be engaged with the ratchet 543a of the ratchet member 543, the recess 551b of the reciprocating member 551 may also be formed such that a first surface 551b1 (specifically, at the distal end 502 side) is formed to have a gentle slope with a predetermined angle, and a second surface 551b2 (specifically, at the proximal end 501 side) may be formed to be vertical or near vertical.

In a state in which the reciprocating member 551 and the ratchet member 543 are coupled to each other (or engaged or in close contact with each other), the inclined first surface 543a1 of the ratchet 543a and the inclined first surface 551b1 of the recess 551b may be formed to face each other (that is, in contact with each other). In addition, the vertically formed second surface 543a2 of the ratchet 543a and the vertically formed second surface 551b2 of the recess 551b may be disposed to face each other (i.e., in contact with each other).

With this configuration, in a state in which the ratchet 543a and the recess 551b are coupled to (or engaged with) each other, the ratchet 543a and the recess 551b may be allowed to move only in one direction, acting as a kind of ratchet.

In an example, when it is assumed that the reciprocating member 551 is in a fixed state, the operation member 540 is movable in a direction in which the second surface 543a2 and the second surface 551b2, which are vertically formed, are away from each other, but when the second surface 543a2 and the second surface 551b2 are in contact with each other, the operation member 540 is not movable in a direction in which the second surface 543a2 and the second surface 551b2 are closer to each other.

In other words, when the reciprocating member 551 is moved toward the distal end 502 in a state in which the reciprocating member 551 and the ratchet member 543 are coupled to each other (or engaged or in close contact with each other), the ratchet member 543 is moved together toward the distal end 502 by the reciprocating member 551. That is, the vertically formed second surface 551b2 of the reciprocating member 551 pushes the vertically formed second surface 543a2 of the operation member 540 such that the ratchet member 543 is moved together toward the distal end 502 by the reciprocating member 551.

In contrast, when the reciprocating member 551 is moved toward the proximal end 501 in a state in which the reciprocating member 551 and the ratchet member 543 are coupled to each other (or engaged or in close contact with each other), only the reciprocating member 551 is moved alone toward the proximal end 501 while the ratchet member 543 is fixed. That is, the inclined first surface 551b1 of the reciprocating member 551 is moved along the inclined first surface 543*al* of the operation member 540 in a state in which the operation member 540 is fixed, so that only the reciprocating member 551 is moved alone toward the proximal end 501.

Figure 19:
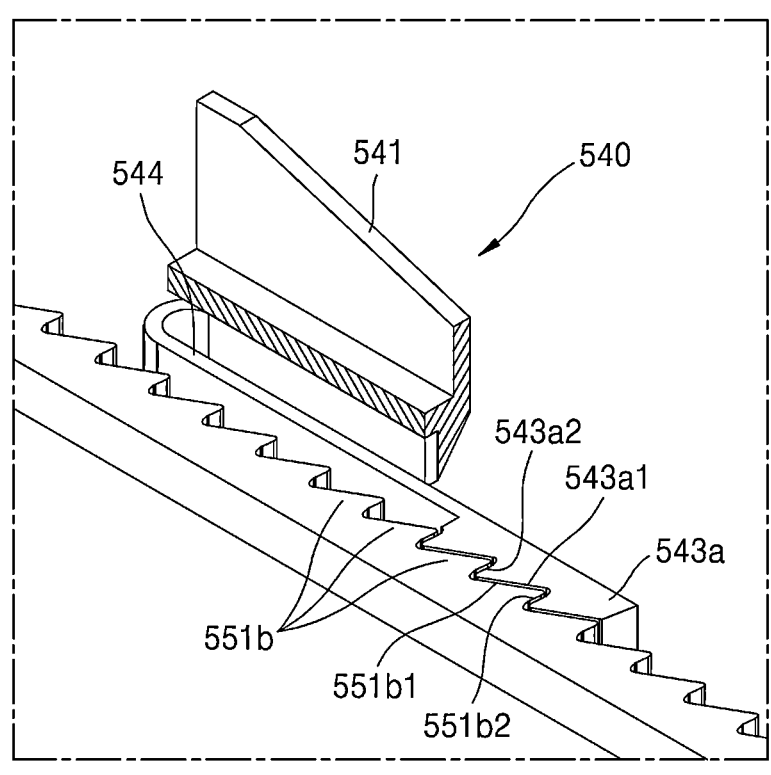
Figure 20:
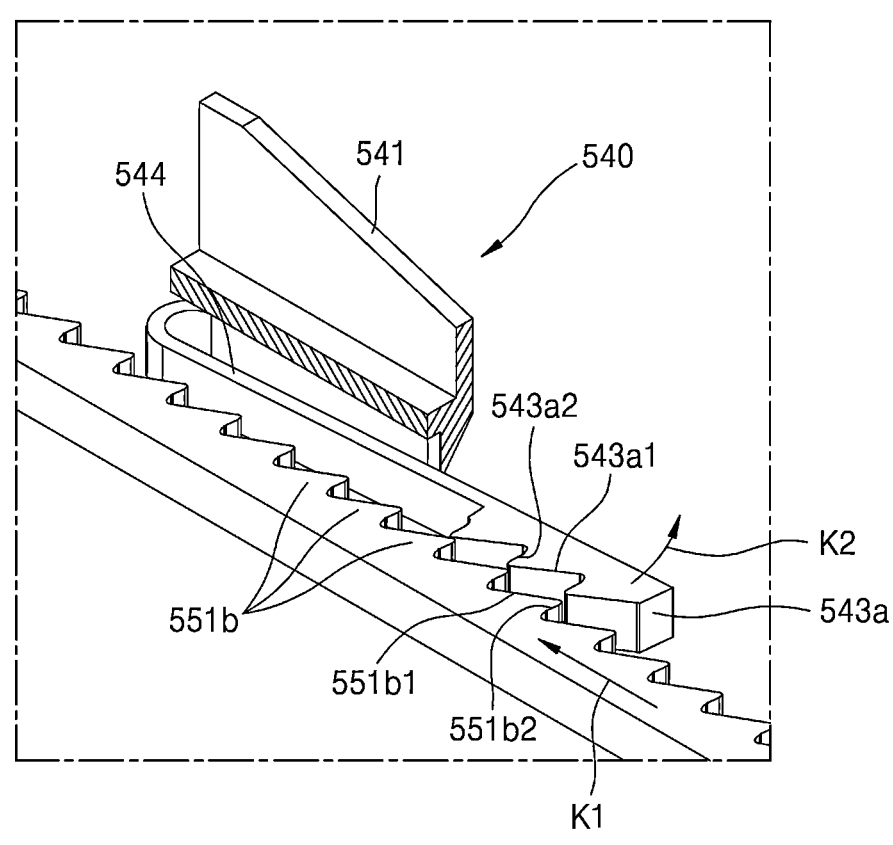

Referring to FIGS. 19 to 22, when the reciprocating member 551 is moved toward (in the direction of an arrow K1 of FIGS. 20 and 21) of the proximal end 501 in the state of FIGS. 19 and 21, as the inclined first surface 551*b*1 of the reciprocating member 551 is moved along the inclined first surface 543*al* of the operation member 540, the ratchet member 543 is pushed as a whole in the direction of an arrow K2 of FIG. 22. In addition, at this time, the elastic member 544 is elastically deformed to a certain extent.

In this state, when the reciprocating member 551 is further moved toward the proximal end 501, and the inclined first surface 551*b*1 of the reciprocating member 551 is moved beyond an end of the inclined first surface 543*al* of the operation member 540, the recess 551*b* of the reciprocating member 551 meets the next ratchet 543*a* of the ratchet member 543. In this case, since the clastic member 544 applies an elastic force in a direction in which the ratchet member 543 comes into close contact with the reciprocating member 551, front surfaces of the reciprocating member 551 and the ratchet member 543 are brought into close contact with each other again.

As a result, the cartridge 500 is accommodated in a cartridge accommodation part 101*a* of the first jaw 101, and in this case, the slot part 551*a* of the reciprocating member 551 of the cartridge 500 is coupled to the staple pulleys 167 and 168 of the end tool 100. Accordingly, the rotational motion of the staple pulleys 167 and 168 of the end tool 100 is converted into a linear motion of the reciprocating member 551 through the slot part 551*a*.

In this case, when the slot part 551*a* of the reciprocating member 551 is connected to the staple pulleys 167 and 168 through the pulley pin 168*a* and the pulley pin 167*a*, and the staple pulleys 167 and 168 are rotated alternately in the clockwise/counterclockwise directions, the reciprocating member 551 may be repeatedly moved forward and backward. In addition, when the reciprocating member 551 is moved forward, the operation member 540 may be moved forward together with the reciprocating member 551, and when the reciprocating member 551 is moved backward, only the reciprocating member 551 may be moved backward and the operation member 540 may remain stationary in place. As the operation member 540 is moved forward while repeating this process, the staple 530 may be stapled by the wedge 541 while the blade 542 cuts stapled tissue.

Hereinafter, a stapling motion of the surgical instrument 10 according to the first embodiment of the present disclosure will be described.

FIGS. 23A to 23C are perspective views illustrating a stapling motion of the end tool of FIG. 14 section by section.

Referring to FIGS. 23A to 23C, in the state as shown in FIG. 23A, as the operation member 540 is moved in the direction of an arrow A1 of FIG. 23B, the wedge 541 of the operation member 540 pushes and raises the withdrawal member 535, and the withdrawal member 535 pushes and raises one side of a lower portion of the staple 530. In addition, due thereto, the staple 530 is ejected to the outside of the first jaw 101 and the cartridge 500.

In this state, when the operation member 540 is further moved in the direction of an arrow A2 of FIG. 23C, the ejected staple 530 is continuously pushed and raised by the operation member 540 while in contact with an anvil (not shown) of the second jaw 102, so that stapling is performed while both end portions of the staple 530 are bent.

As such motions are continuously performed, stapling is sequentially performed in the plurality of staples 530 from the staple 530 at the proximal end 501 side to the staple 530 at the distal end 502 side.

(Backward-Moving Wire Structure)

The surgical instrument 10 according to the first embodiment of the present disclosure includes the backward-moving wire 309 and various structures related thereto.

Figure 24:
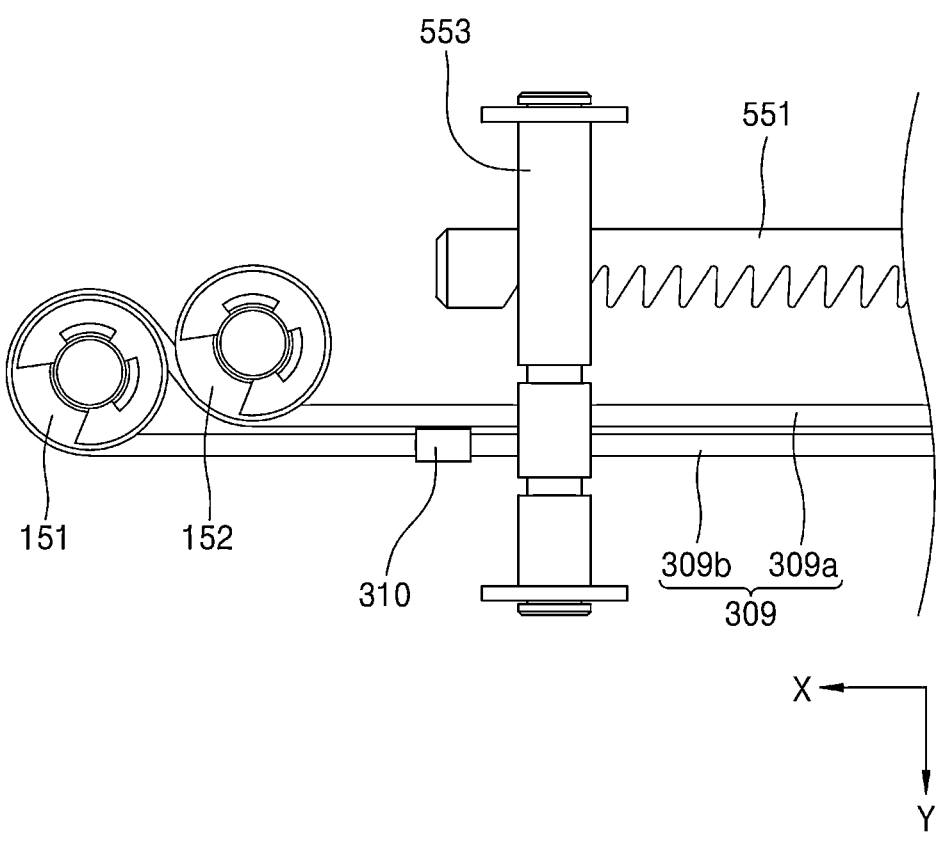
FIG. 24 is a plan view illustrating a distal end of the end tool of FIG. 4.
Figure 25:
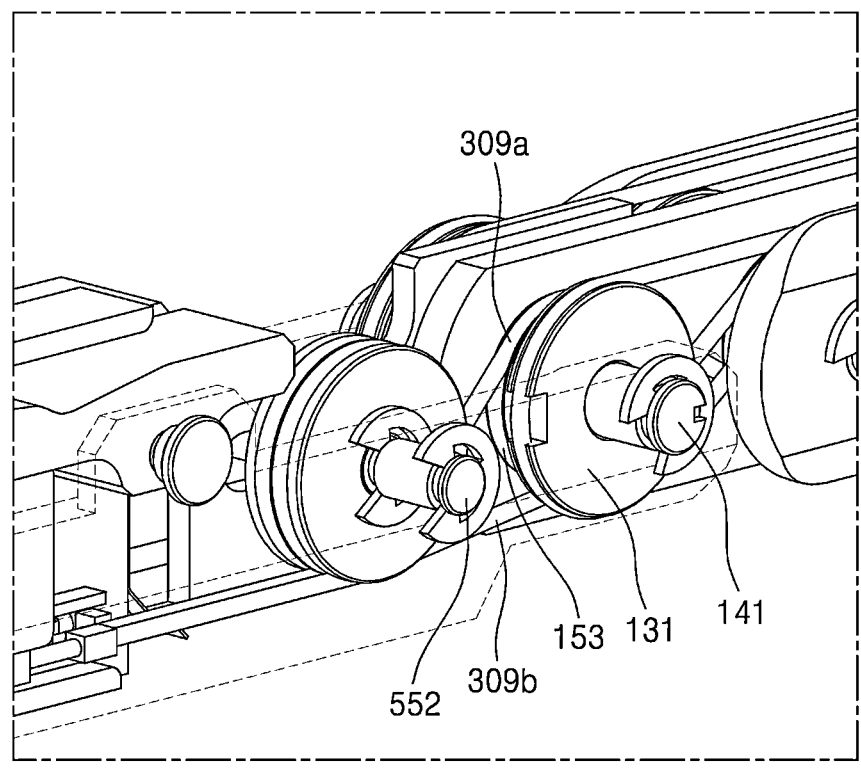
FIG. 25 is a perspective view illustrating a jaw rotation shaft and pulleys of the end tool of FIG. 3.
Figure 26:
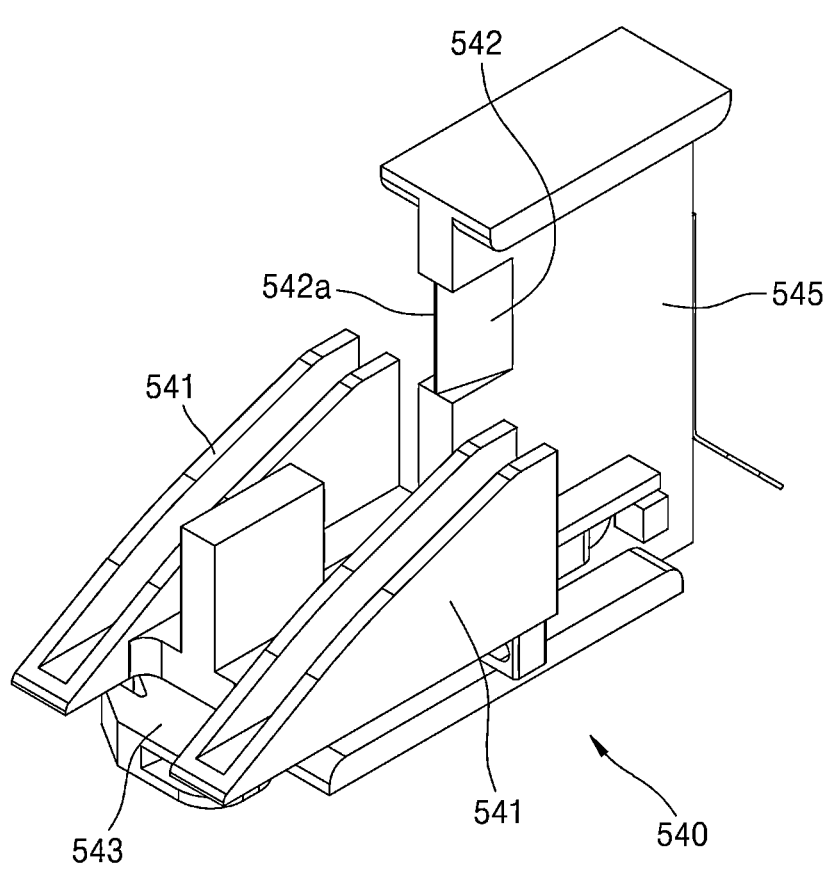
FIGS. 26 to 28 are perspective views illustrating the operation member of FIG. 3.
Figure 27:
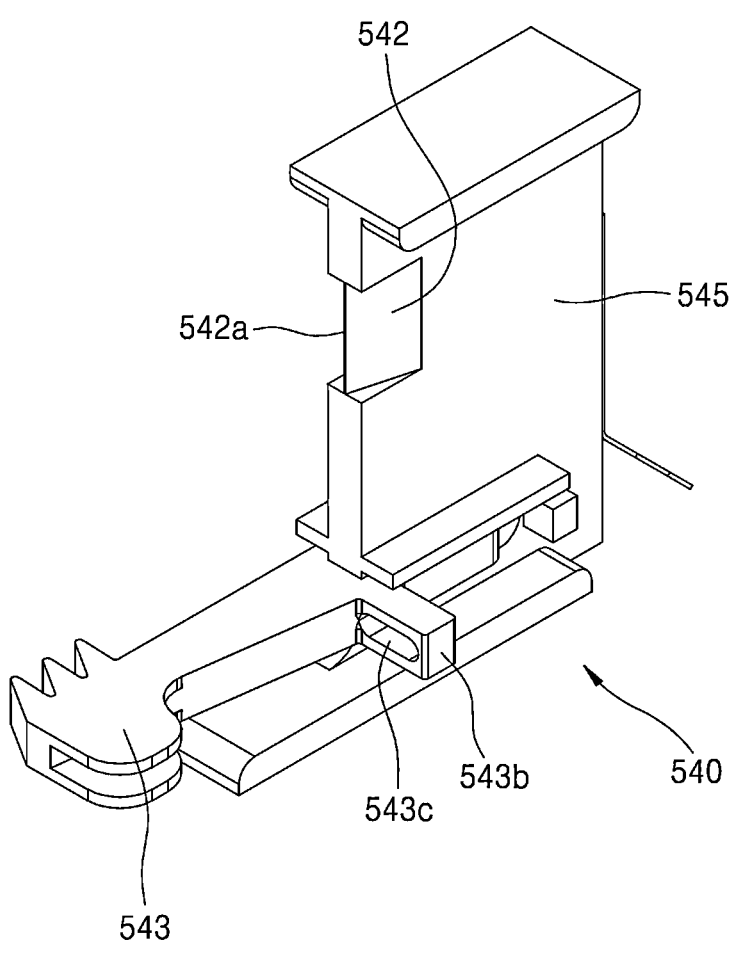
Figure 28:
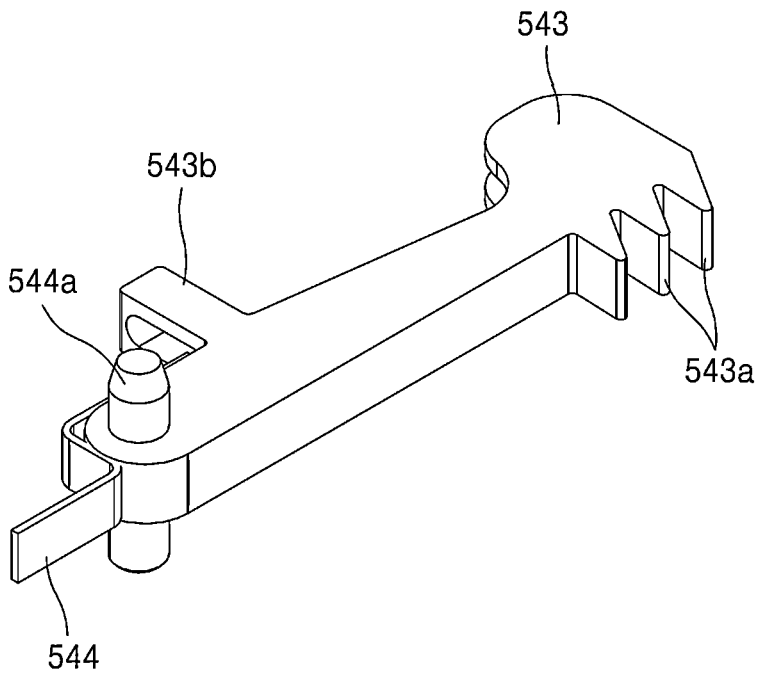

FIGS. 3 and 4 are plan views illustrating the first jaw of the end tool of the surgical instrument according to the first embodiment of the present disclosure. FIG. 24 is a plan view illustrating the distal end of the end tool of FIG. 4, FIG. 25 is a perspective view illustrating the jaw rotation shaft and the pulleys of the end tool of FIG. 3, and FIGS. 26 to 28 are perspective views illustrating the operation member of FIG. 3.

Referring to FIGS. 3 and 4 and FIGS. 24 and 25 again, the end tool 100 according to the first embodiment of the present disclosure may include the backward-moving wire structure to move the operation member 540 that has moved forward toward the distal end backward toward the proximal end.

Various methods may be devised to move the operation member 540 backward, such as fixing a wire directly to the operation member 540 and pulling the wire toward the proximal end to move the operation member 540 backward. However, when the wire is fixed to the operation member 540, the wire may interfere with the forward movement of the operation member 540. Thus, there is a need for a structure that is not fixed to the operation member 540 but can move the operation member 540 backward by moving the wire backward.

Accordingly, in the surgical instrument 10 according to the first embodiment of the present disclosure, the backward-moving wire 309 may be formed in the first jaw 101 as an independent structure that is not fixed to the operation member 540.

Here, the wire for moving the operation member 540 backward will be referred to as the backward-moving wire 309. The backward-moving wire may be disposed parallel to the longitudinal direction of the first jaw 101, i.e., a forward and backward movement direction of the operation member 540. In order to dispose the backward-moving wire 309, the backward-moving wire pulley 151 may be positioned at the distal end side of the first jaw 101.

The backward-moving wire 309 may be formed to extend from the proximal end side of the end tool 100 to the backward-moving wire pulley 151, where the backward-moving wire 309 is wound around and redirected by 180 degrees before being directed back toward the proximal end of the end tool 100. That is, the backward-moving wire 309 may be described as having two strands disposed in the longitudinal direction of the first jaw 101. Here, for convenience of description, the two strands of the backward-moving wire will be divided, and one strand closer to the operation member 540 will be referred to as an inner side wire 309*a* and another strand will be referred to an outer side wire 309*b*.

Meanwhile, the backward-moving wires 309*a* and 309*b*, which are wound around the backward-moving wire pulley 151 and emerge in two strands, may be spaced apart from each other by approximately a diameter of the pulley 151. At this time, the inner side wire 309*a* may be disposed as close as possible to the outer side wire 309*b* by providing an auxiliary pulley 152 at a position close to the backward-moving wire pulley 151 as illustrated in FIG. 24.

That is, by disposing the auxiliary pulley 152, which is axially coupled to a rotation shaft parallel to the rotation shaft of the backward-moving wire pulley 151 and rotates on the same plane as the backward-moving wire pulley 151, in close proximity to the backward-moving wire pulley 151 and allowing the inner side wire 309a to pass while coming into contact with a portion of the auxiliary pulley 152, the path of the inner side wire 309a may be changed so that the inner side wire 309a approaches the outer side wire 309b. However, the concept of the present disclosure is not limited thereto, and the auxiliary pulley 152 may be disposed by setting a path for the outer side wire 309b to approach the inner side wire 309a, and the size and arrangement form of each pulley may vary.

The backward-moving wire 309 of the end tool 100 according to the first embodiment of the present disclosure may include a coupling member 310. Here, with the wire inserted into the coupling member 310, the coupling member 310 may be crimped and fixed to be coupled to the wire.

As described above, the coupling member 310 has a protruding shape fixed to a portion of the backward-moving wire 309 and may be moved forward or backward in the longitudinal direction of the first jaw 101 in response to the movement of the backward-moving wire 309.

Accordingly, when the backward-moving wire 309 to which the coupling member 310 is coupled is moved toward the proximal end and the coupling member 310 interferes with a portion of the operation member 540, the coupling member 310 may push and move the operation member 540 backward toward the proximal end. The principle of moving the operation member 540 backward by bringing the coupling member 310 into contact with the operation member 540 will be described in detail later.

Meanwhile, the coupling member 310 may not be moved when moving the operation member 540 toward the distal end of the end tool 100, and may be moved toward the proximal end when moving the operation member 540 backward.

Here, the coupling member 310 may be configured to be disposed at the distal end side of the end tool 100 to avoid interference with the operation member 540 until the operation member 540 moves forward to the end of the distal end.

Referring to FIG. 25 or the like, the surgical instrument 10 according to the first embodiment of the present disclosure may further include the loop pulleys 153 and 154 coupled to the jaw rotation shaft 141 of the end tool 100.

Here, the loop pulleys 153 and 154 as well as the pitch pulley 131 and staple pulleys 167 and 168 may be coupled to the rotation shaft 141, and these pulleys may be divided and disposed on both sides of one end portion of the end tool hub 180. In an example, the loop pulleys 153 and 154 and the pitch pulley 131 may be disposed on one side surface of one end portion of the end tool hub 180, and the staple pulleys 167 and 168 may be disposed on another side surface thereof.

The loop pulleys 153 and 154 may be pulleys that have the same diameter and are rotatable independently of each other. The inner side wire 309a, which is one of two strands of the backward-moving wire 309, may be connected to the loop pulley 153, and the outer side wire 309b may be connected to the loop pulley 154.

In addition, the inner side wire 309a and the outer side wire 309b may be respectively wound around the pulleys in different directions with respect to the jaw rotation shaft 141. In an example, the inner side wire 309a may be disposed to pass above the pulley 153 with respect to the jaw rotation shaft 141, and the outer side wire 309b may be disposed to pass below the pulley 154 with respect to the jaw rotation shaft 141. Of course, the arrangement may be reversed.

The backward-moving wire 309 may be pre-tensioned by forming a loop by connecting the backward-moving wire 309 from the backward-moving wire pulley 151 to the loop pulleys 153 and 154 at the proximal end side as described above. That is, the backward-moving wire 309 may be prevented from separating from the pulley at the joint portion at which the end tool 100 rotationally moves.

In addition, when the first jaw 101 of the end tool 100 rotationally moves around the jaw rotation shaft 141, the backward-moving wire 309 passing through the rotation shaft 141 should be wound or unwound when an angle of the first jaw 101 is changed, and this change in length of the backward-moving wire 309 may be automatically compensated for.

In other words, as the backward-moving wires 309 are configured to be wound in opposite directions respectively around the loop pulley 153 and the loop pulley 154, the backward-moving wires 309 may be maintained in pre-tension as one wire is wound as much as another wire is unwound. However, as the backward-moving wire 309 is moved when the first jaw 101 rotates around the rotation shaft 141, the coupling member 310 fixed to the backward-moving wire 309 is also moved, and thus the coupling member 310 may be disposed by securing a clearance space so as not to interfere with the operation member 540.

Hereinafter, the principle of moving the operation member 540 backward by bringing the coupling member 310 into contact with the operation member 540 will be described.

Describing the operation member 540 first, the operation member 540 according to the first embodiment of the present disclosure may include the ratchet member 543.

The ratchets 543a may be formed on one surface of the ratchet member 543, which is in contact with the reciprocating member 551, and as described above, the ratchet 543a may be a portion engaged with the recess 551b of the reciprocating member 551.

In addition, a protrusion 543b may be formed on a surface of the ratchet member 543, which is opposite to the surface on which the ratchets 543a are formed. That is, the protrusion 543b may be formed on a side of the ratchet member 543 away from the reciprocating member 551. In addition, the protrusion 543b may be formed close to a rotation shaft 544a which is the center of rotation of the ratchet member 543.

In addition, the backward-moving wire 309 and the coupling member 310 may be positioned on the opposite side of the reciprocating assembly 550 with respect to the ratchet member 543. That is, the backward-moving wire 309 and the coupling member 310 may be disposed close to the protrusion 543b of the ratchet member 543.

Meanwhile, as described above, when the backward-moving wire 309 is moved, causing the coupling member 310 to move from the distal end side toward the proximal end and come into contact with the operation member 540, the coupling member 310 may come into contact with the protrusion 543b of the ratchet member 543. At this time, when the backward-moving wire 309 is further moved so that the coupling member 310 pushes the protrusion 543b toward the proximal end, a rotational force that allows the ratchet member 543 to rotate around the rotation shaft 544a of the ratchet member 543 is applied, and eventually, the ratchet member 543 may be moved in a direction away from the reciprocating member 551. Thereafter, the recess 551b of the reciprocating member 551 and the ratchet 543a of the ratchet member 543 are in a spaced-apart state, allowing the operation member 540 including the ratchet member 543 to move backward toward the proximal end without interference from the reciprocating member 551.

In addition, a hollow 543*c* may be formed at a center portion of the protrusion 543*b* of the ratchet member 543. Specifically, the hollow 543*c* passing through the protrusion 543*b* in a direction parallel to the path in which the operation member 540 linearly moves in the first jaw 101 may be formed in the protrusion 543*b*. Further, the backward-moving wire 309 may pass through the hollow 543*c*. However, the coupling member 310 fixed to the backward-moving wire 309 may be formed to interfere with the protrusion 543*b* without passing through the hollow 543*c* when the backward-moving wire 309 is moved.

Thus, the movement of the backward-moving wire 309 may cause the coupling member 310 to press the protrusion 543*b* toward the proximal end. That is, as described above, the ratchet 543*a* of the ratchet member 543 may be spaced apart from the reciprocating member 551 so that the operation member 540 including the ratchet member 543 may be moved backward toward the proximal end without interference from the reciprocating member 551.

Here, at least one of the inner side wire 309*a* and the outer side wire 309*b* of the backward-moving wire 309 may be formed to pass through the inside of the hollow 543*c*. Alternatively, both the inner side wire 309*a* and the outer side wire 309*b* may be formed to pass through the inside of the hollow 543*c*. Here, the coupling member 310 may be coupled to the outer side wire 309*b*. When the coupling member 310 is coupled to the outer side wire 309*b* and presses the protrusion 543*b*, a greater rotational force causing the ratchet member 543 to rotate around the rotation shaft 544*a* may be applied.

Figure 29A:
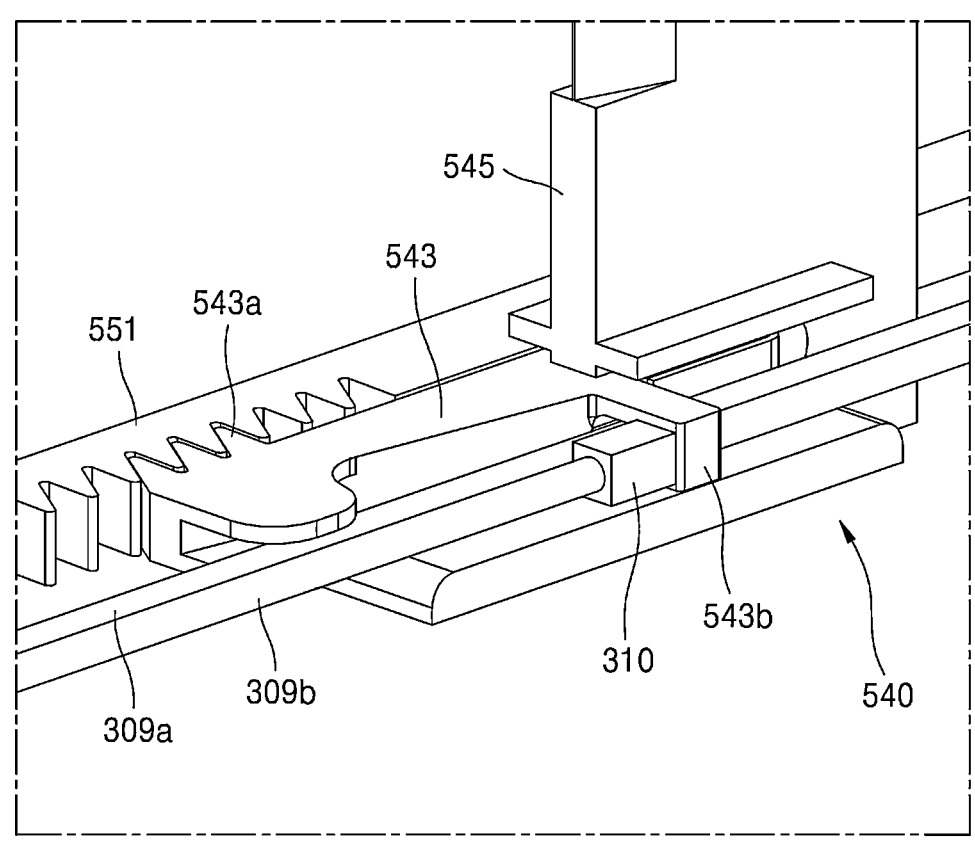
FIGS. 29A to 32 are views for describing a backward-movement prevention structure of the surgical instrument according to the first embodiment of the present disclosure.
Figure 29B:
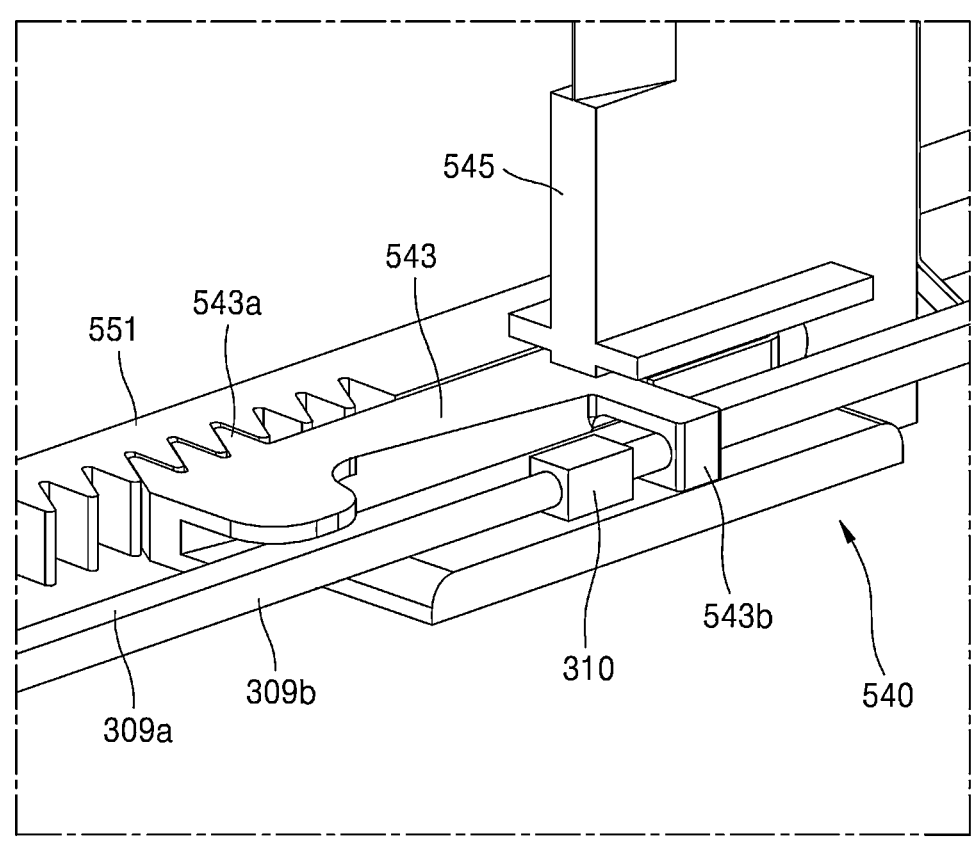

Meanwhile, the coupling member 310 may be formed to remain at the distal end side of the end tool, but as illustrated in FIG. 29A, the coupling member 310 may also be formed to move forward together with the operation member 540 at the front surface of the operation member 540 while the operation member 540 moves forward toward the distal end of the end tool. However, the coupling member 310 may be formed to move forward together with the operation member 540 while securing a clearance space by being spaced apart from the operation member 540 such that the coupling member 310 does not interfere with the forward movement of the operation member 540 (refer to FIG. 29B).

When the coupling member 310 is configured to move forward together with the operation member 540 at the front surface of the operation member 540 as described above, the coupling member 310 may quickly come into contact with the operation member 540 to initiate the backward movement. For example, when the operation member 540 is not moved to the end of the distal end side of the end tool, but is interrupted in forward movement and is moved backward, initiating the backward movement can be made faster when the coupling member 310 is moved adjacent to the operation member 540, compared to when the coupling member 310 is allowed to remain at the distal end.

In addition, when the coupling member 310 is configured to move together with the operation member 540 at the front surface of the operation member 540 as described above, a backward-movement prevention structure may be implemented at the same time, which will be described later.

Meanwhile, when the reciprocating member 551 is moved forward toward the distal end and then moved backward toward the proximal end, the operation member 540 may be unintentionally moved backward due to a frictional force generated between the recess 551*b* of the reciprocating member 551 and the ratchet 543*a* of the ratchet member 543.

The backward-movement prevention structure of the operation member 540 for preventing such a backward movement will be described below.

FIGS. 29A to 32 are views for describing the backward-movement prevention structure of the surgical instrument according to the first embodiment of the present disclosure.

Figure 30:
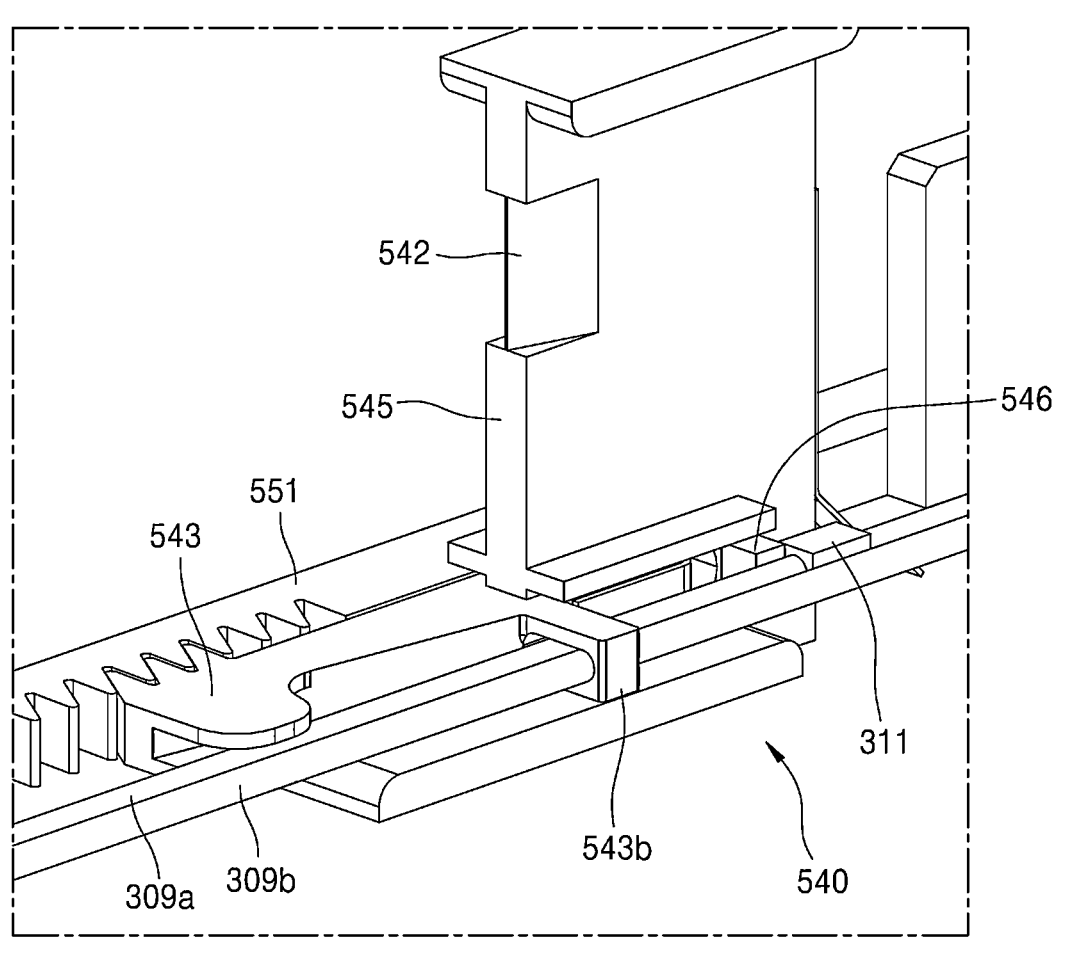
Figure 31:
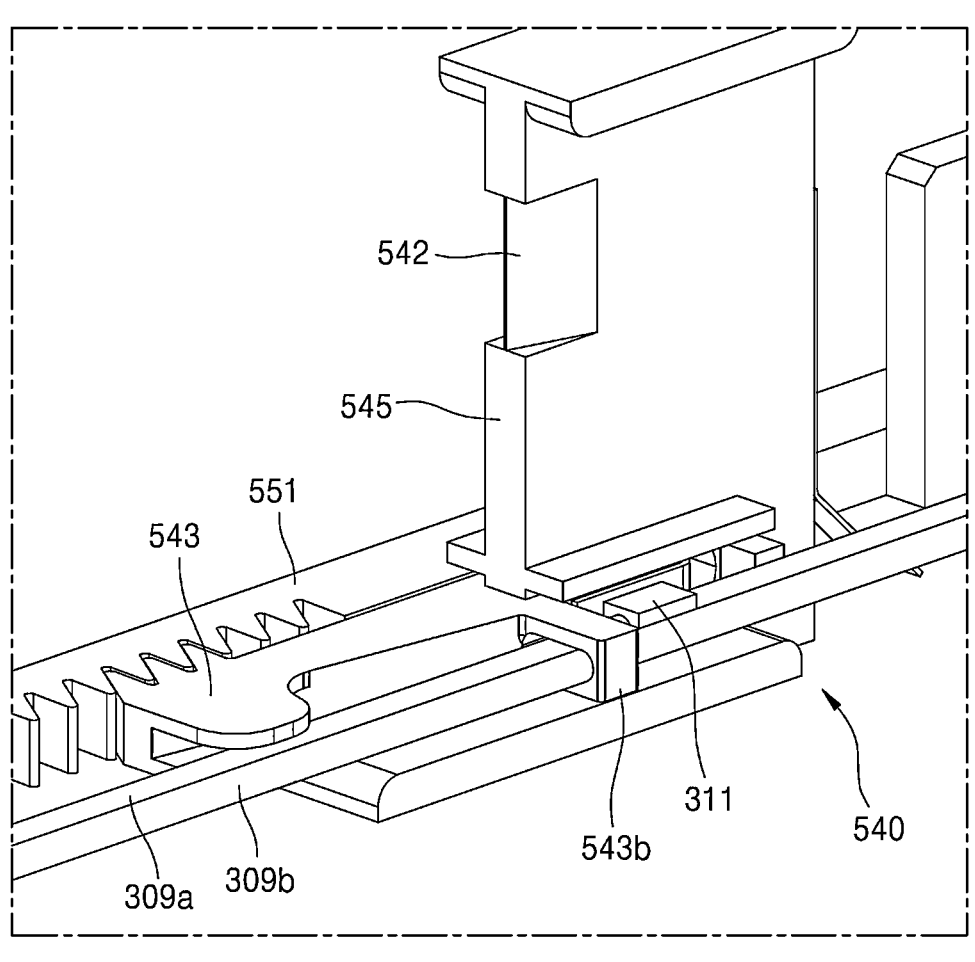
Figure 32:
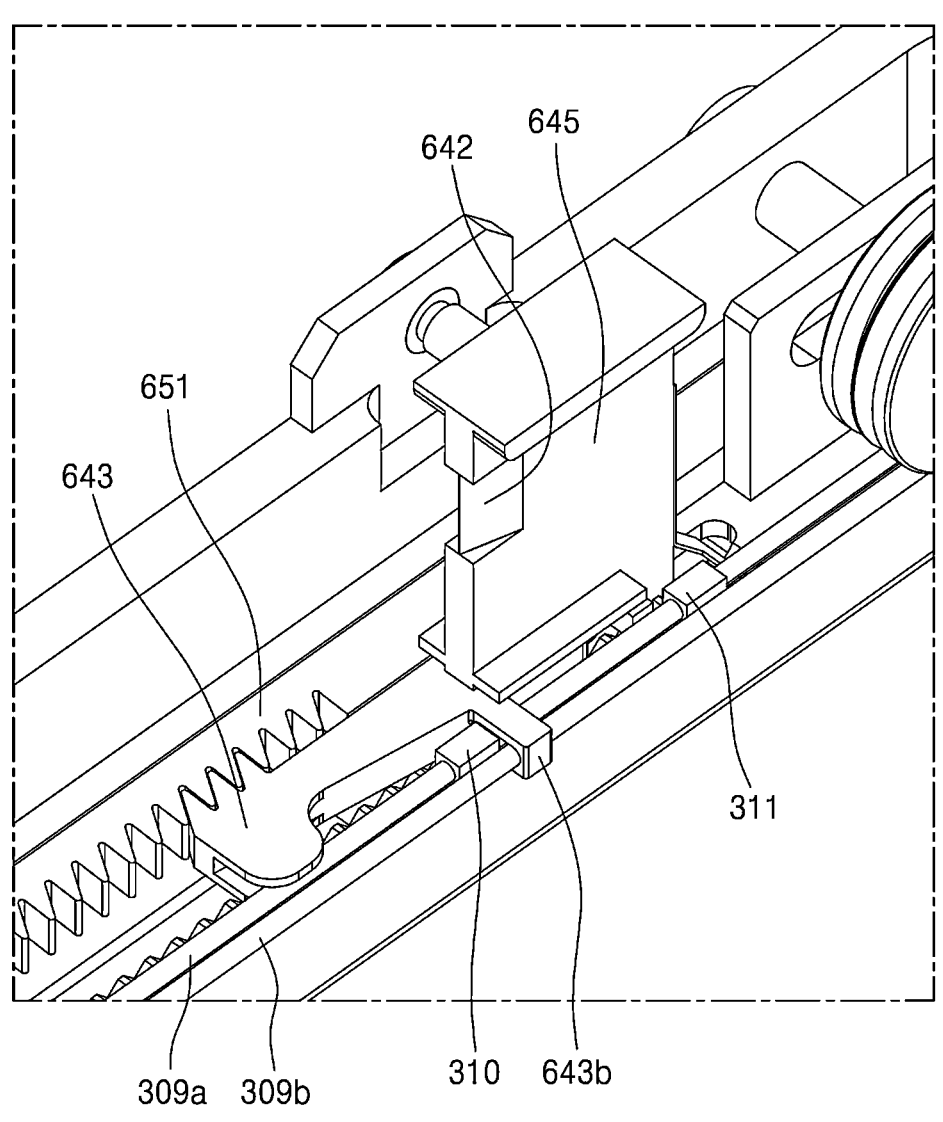

Referring to FIG. 30, the body 545 of the operation member 540 may include a protrusion 546 protruding toward the backward-moving wire 309.

The protrusion 546 of the body 545 may be formed to be in contact with a coupling member 311, which is coupled to the backward-moving wire 309, but does not interfere with the movement of the backward-moving wire 309. That is, the backward-moving wire 309 and the protrusion 546 are formed to be spaced apart from each other, but the coupling member 311 and the protrusion 546 may be formed to partially come into contact with each other. In addition, when attempting to partially move the operation member 540 backward, the coupling member 311 in contact with the protrusion 546 may prevent the operation member 540 from moving toward the proximal end.

To this end, the coupling member 311 should be disposed on the rear surface of the protrusion 546. In this case, as the operation member 540 moves forward toward the distal end, the coupling member 311 may be moved together with the operation member 540 at the rear surface of the operation member 540 while being spaced apart from the operation member 540 to secure a clearance space.

Alternatively, as the operation member 540 moves forward toward the distal end, the coupling member 311 may be moved together with the operation member 540 at the rear surface of the operation member 540 while applying a force to the operation member 540 in a forward-moving direction. That is, when the operation member 540 is moved forward toward the distal end of the end tool due to the forward and backward reciprocating linear motion of the reciprocating member 551, the coupling member 311 of the backward-moving wire 309 is also moved forward together with the operation member 540 while weakly pushing the protrusion 546 from the rear surface of the protrusion 546, but when the operation member 540 is intended to move backward due to the frictional force with the reciprocating member 551, the coupling member 311 may exert a strong resistance against the protrusion 546.

Meanwhile, the coupling member 311, which is coupled to the backward-moving wire 309 to prevent the backward movement, may be disposed on the rear surface of the protrusion 543*b* of the ratchet member 543. In addition, as described above, the backward-moving wire 309 may be formed to pass through the hollow 543*c* formed in the protrusion 543*b* of the ratchet member 543, and the coupling member 311 may be formed not to pass through the hollow 543*c*. As described above, the coupling member 311 is formed to interfere with the protrusion 543*b* of the ratchet member 543, and thus the backward movement of the operation member 540 may be prevented by the coupling member 311 when the operation member 540 is intended to move backward.

Meanwhile, the coupling member 311, which is coupled to the backward-moving wire 309 to prevent the backward movement, may be coupled to the inner side wire 309*a* or the outer side wire 309*b*. Preferably, the coupling member 311 may be coupled to the inner side wire 309*a*.

The surgical instrument 10 according to the first embodiment of the present disclosure includes the backward-movement prevention structure utilizing the backward-moving wire 309, and in this case, the backward-movement prevention structure may include both the coupling member 310 for the backward movement of the operation member 540 and the coupling member 311 for preventing the backward movement of the operation member 540. Here, the coupling member 310 and the coupling member 311 may be coupled to the inner side wire 309*a* or the outer side wire 309*b*, but both must be coupled to the same wire. In other words, both the coupling member 310 for the backward movement of the operation member 540 and the coupling member 311 for preventing the backward movement of the operation member 540 must be moved in the same direction.

Specifically, the coupling member 310 is disposed to move forward together with the operation member 540 at the front surface of the operation member 540 while the operation member 540 moves forward toward the distal end of the end tool, and the coupling member 311 may be disposed to move forward together with the operation member 540 at the rear surface of the protrusion 546 of the operation member 540 or the rear surface of the protrusion 543*b* of the ratchet member 543.

In this manner, in the surgical instrument 10 according to the first embodiment of the present disclosure, the operation member 540 is prevented from being unintentionally moved backward, and can be moved backward when required.

Meanwhile, although the linear motion of the reciprocating member 551 by the interaction between the reciprocating member 551 including the slot part 551*a* and the staple pulleys 167 and 168, and a resulting forward movement of the operation member 540 have been described in the present embodiment, the technical idea of the backward-moving wire structure of the first embodiment of the present disclosure is not limited thereto, and may be applied in conjunction with various methods for a stapling motion.

Modified Example of First Embodiment

Hereinafter, an end tool 100 of a surgical instrument according to a modified example of the first embodiment of the present disclosure will be described. Here, the end tool 100 of the surgical instrument according to the modified example of the first embodiment of the present disclosure is different from the end tool (see 100 of FIG. 1 or the like) of the surgical instrument according to the first embodiment of the present disclosure described above in that the configuration of the backward-movement prevention structure of the operation member 540 is changed. Such a configuration that is changed from that of the first embodiment will be described in detail below.

Figure 33:
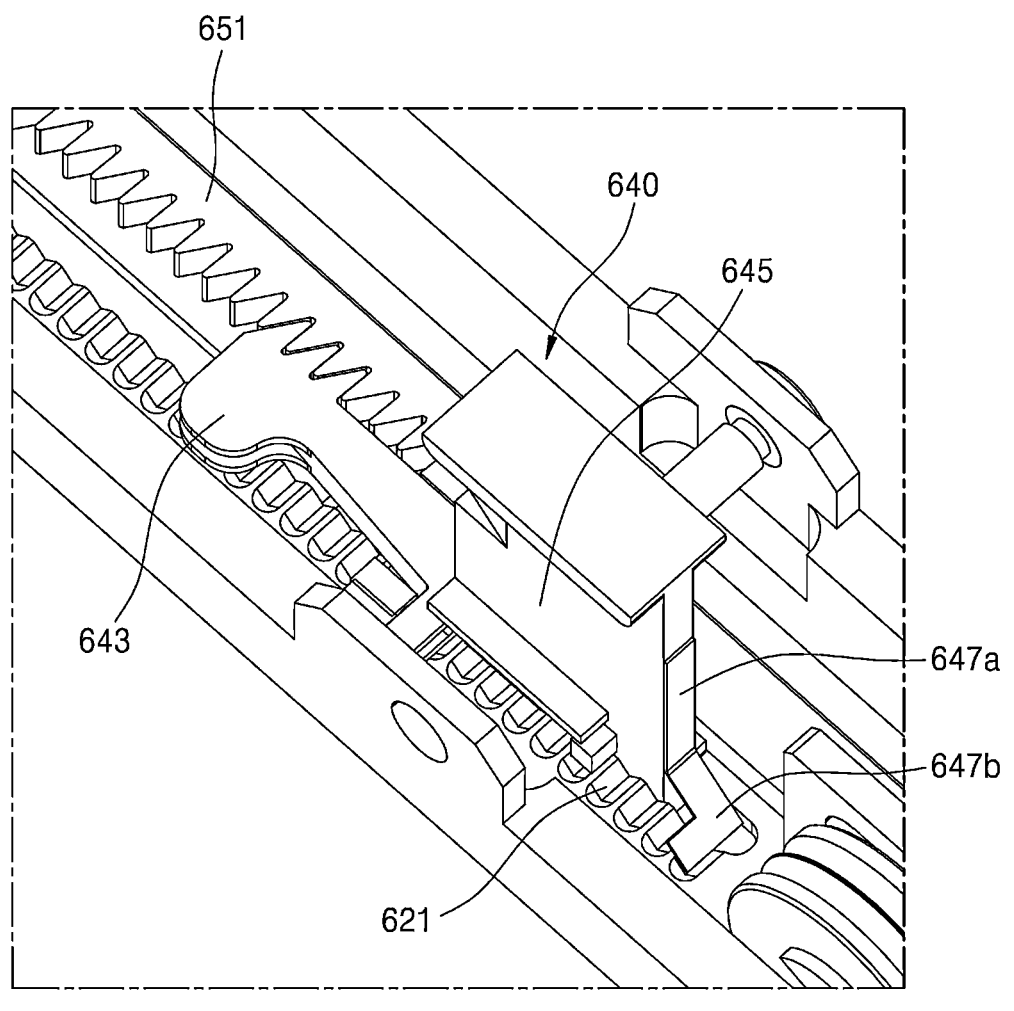
FIG. 33 is a perspective view illustrating an operation member of a surgical instrument according to a modified example of the first embodiment of the present disclosure.
Figure 34:
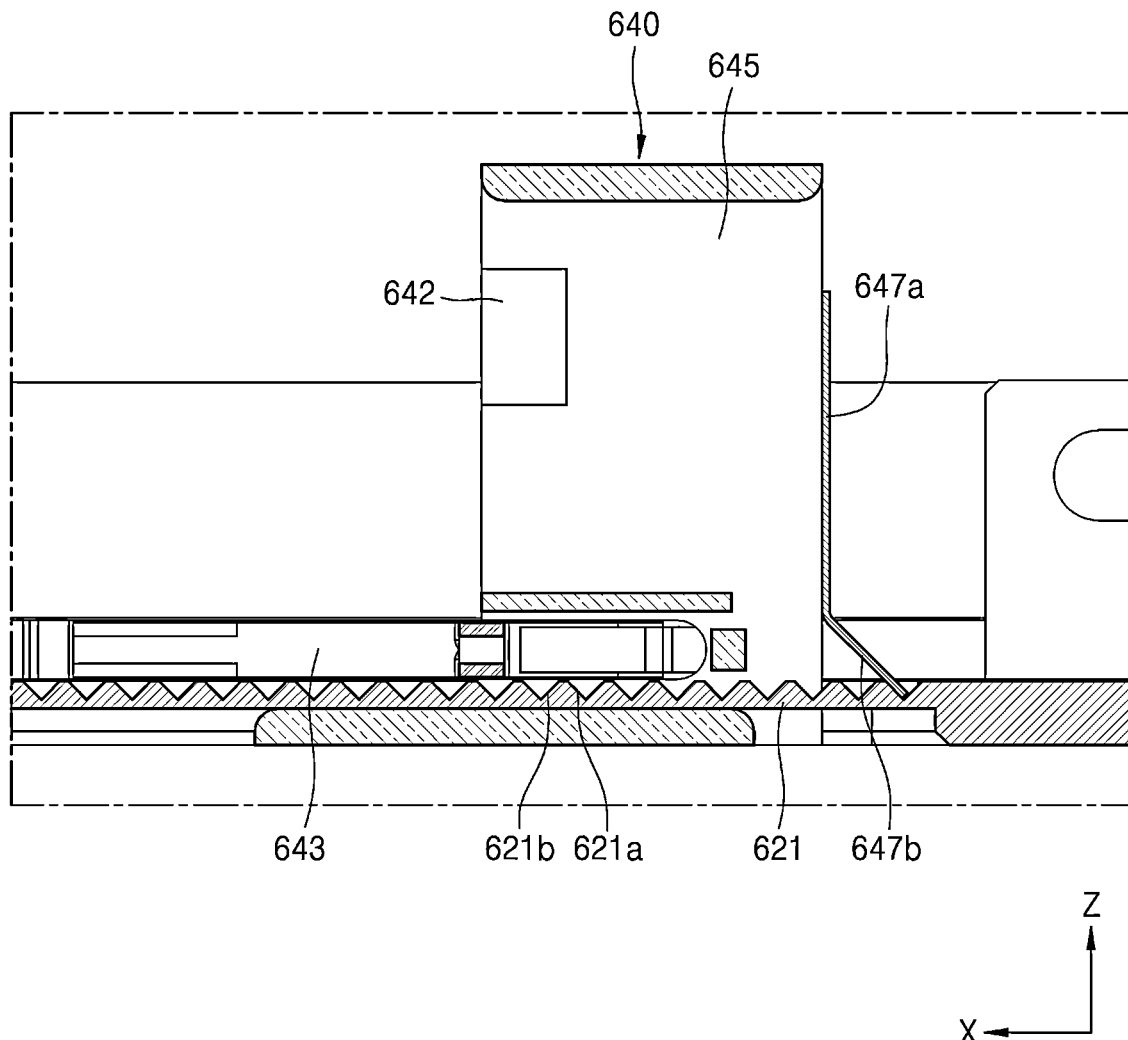
FIG. 34 is a side cross-sectional view illustrating the operation member of FIG. 33.

FIG. 33 is a perspective view illustrating a first jaw 101 including an operation member 640 of the surgical instrument according to the modified example of the first embodiment of the present disclosure. FIG. 34 is a side cross-sectional view illustrating the operation member 640 of FIG. 33, and FIG. 35 is a perspective view illustrating the operation member 640 and the backward-moving wire structure of FIG. 33.

Figure 35:
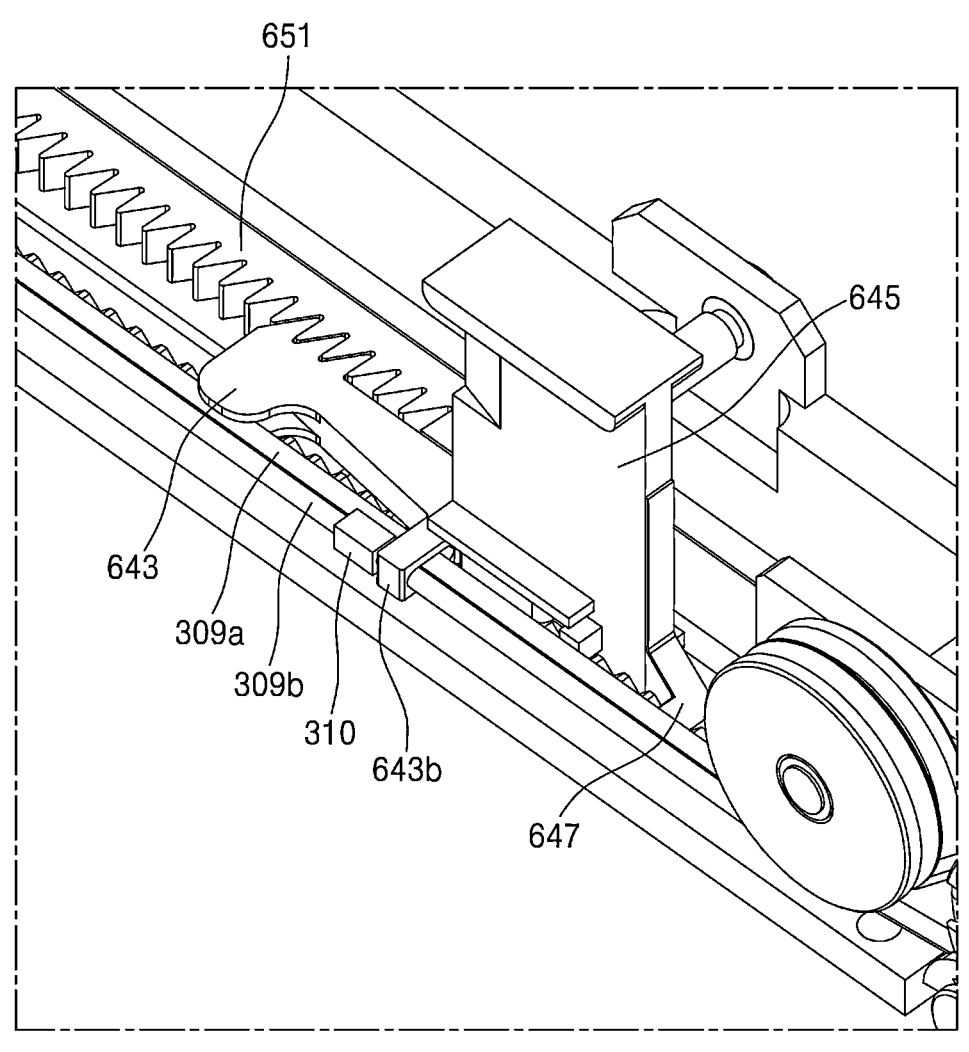
FIG. 35 is a perspective view illustrating the operation member and the backward-moving wire structure of FIG. 33.

Referring to FIGS. 33 to 35, the first jaw 101 according to the modified example of the first embodiment of the present disclosure may include a reciprocating member 651 of a reciprocating assembly (not shown), the operation member 640, and the like. In addition, although not shown in the drawing, a cartridge 600 accommodated in an accommodation part of the first jaw 101, and a cover 610, a housing 620, and the like of the cartridge may be included.

Here, the reciprocating assembly (not shown) is substantially the same as the reciprocating assembly 550 according to the first embodiment of the present disclosure, and thus a detailed description thereof will be omitted.

Meanwhile, the housing 620 forms an outer shape of the cartridge 600, and may be formed entirely in the form of a hollow box with one surface (upper surface) removed to accommodate the reciprocating assembly (not shown), the operation member 640, and the staples (see 530 of FIG. 10) therein. Here, the housing 620 may be formed in an approximately "U" shape in cross section.

One or more recesses 621 may be formed on an inner side surface of the housing 620 in a region contactable with the operation member 640. Alternatively, one or more recesses 621 may be formed on an inner side surface of the first jaw 101 in a region contactable with the operation member 640. Alternatively, the recesses 621 may be described as being formed below a moving path of the operation member 640.

The one or more recesses 621 may be formed in a wedge shape. In other words, it may also be described that the one or more recesses 621 include a slope formed to have a greater height at the distal end side of the cartridge 600 than the proximal end side.

Here, each of the one or more recesses may include a first inclined surface 621*a*, which is a surface at a proximal end side, and a second inclined surface 621*b*, which is a surface at a distal end side. The first inclined surface 621*a* may be formed to have a gentle slope, and the second inclined surface 621*b* may be formed to be near vertical.

The recesses 621 may be formed to be in contact with a snap 647 of the operation member 640 to prevent a backward movement of the operation member 640 (that is, the movement toward the proximal end). This will be described in more detail later.

The operation member 640 according to the modified example of the first embodiment of the present disclosure may include a body 645, a blade 642, a ratchet member 643, and the snap 647. In addition, although not shown in the drawings, the operation member 640 may include a wedge 641 similar to the operation member 540 according to the first embodiment.

The body 645, the blade 642, the ratchet member 643, and the wedge 641 of the operation member 640 according to the modified example of the first embodiment of the present disclosure are substantially the same as the body 545, the blade 542, the ratchet member 543, and the wedge 541 of the operation member 540 according to the first embodiment of the present disclosure, and thus detailed descriptions thereof will be omitted.

Meanwhile, the snap 647 may be formed to protrude from any one side of the body 645 or the wedge 641. In addition, the snap 647 is formed as a plate-shaped member, and may be formed to be in contact with the inner side surface of the housing 620 or the inner side surface of the first jaw 101. In detail, one end portion 647*a* of the snap 647 may be coupled to a lower end of a rear surface of the operation member 640, and the other end portion 647*b* of the snap 647 may be in contact with the recess 621.

In this case, the snap 647 may be formed to be engaged with the recess 621 of the housing 620 or the first jaw 101. When the snap 647 is engaged with the recess 621, the operation member 640 may be prevented from moving backward (i.e., moving toward the proximal end) due to the snap 647 and the recess 621.

Here, the snap 647 may be formed to be elastically deformable to a certain extent. That is, the snap 646 may serve as a kind of leaf spring. Accordingly, when the snap 647 is moved along the inclined surface of the recess 621, the snap 647 may be elastically deformed to a certain extent toward the body 645. In addition, when the snap 647 is brought into contact with the next recess 621 beyond the inclined surface of the recess 621, the snap 647 may be elastically restored toward the housing 620.

Specifically, when the operation member 640 moves forward toward the distal end, the snap 647 is moved up along the first inclined surface 621a and moved toward the distal end. When the reciprocating assembly (not shown) moves backward toward the proximal end, the snap 647 interferes with the second inclined surface 621b to prevent the operation member 640 from moving backward toward the proximal end.

Here, when the reciprocating member 651 moves backward, only the reciprocating member 651 may be moved backward and the operation member 640 may more securely remain stationary in place. That is, the operation member 640 may be more securely prevented from moving toward the proximal end of the end tool 100 by the snap 647 and the recesses 621.

Meanwhile, the surgical instrument according to the modified example of the first embodiment of the present disclosure may include a backward movement structure including the backward-moving wire 309 as in the surgical instrument according to the first embodiment of the present disclosure.

Referring to FIG. 35, the coupling member 310 coupled to the outer side wire 309b may be formed to be in contact with a protrusion 643b of the ratchet member 643 and may move the operation member 640 toward the proximal end in response to the movement of the backward-moving wire 309.

Here, when the operation member 640 is moved backward toward the proximal end by the backward-moving wire 309, the snap 647 may be plastically deformed and may lose a function thereof to prevent the backward movement of the operation member 640. That is, during linear reciprocation of the reciprocating member 651 and a resulting forward movement of the operation member 640, in order to prevent an unintended backward movement of the operation member 640, the snap 647 may interfere with the recess 621 so that the operation member 640 may not be moved forward. Whereas, during reversing operation to move the operation member 640 toward the proximal end, a strong reversing force is transmitted through the coupling member 310 of the backward-moving wire 309, which can cause the snap 647 to deform plastically and lose the function thereof to prevent the backward movement.

The present disclosure has been described above in relation to its preferred embodiments. It will be understood by those skilled in the art that various changes in form and details may be made therein without departing from the essential features of the present disclosure. Therefore, the disclosed embodiments should be considered in descriptive sense only and not for purposes of limitation. The scope of the present disclosure is defined not by the detailed description of the disclosure but by the appended claims, and all differences within the scope will be construed as being included in the present disclosure.

A surgical instrument according to the present disclosure can facilitate a stapling motion and improve the usability thereof by including a mechanism for preventing a backward movement of the operation member during a stapling motion and a backward-moving wire structure for the backward movement of the operation member.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A surgical instrument comprising:
an end tool including one or more jaws and rotatable in at least one direction,
wherein one jaw of the one or more jaws includes:
a reciprocating assembly disposed in the one jaw and movable in a first direction, which is a longitudinal direction of the one jaw, with respect to the one jaw;
an operation member disposed on one side of the reciprocating assembly, the operation member being capable of contacting the reciprocating assembly and movable forward toward a distal end of the one jaw from a proximal end side of the one jaw in the first direction by the reciprocating assembly; and
a backward-moving wire disposed adjacent to the operation member, the backward-moving wire being movable in the first direction,
wherein the backward-moving wire includes one or more coupling members fixed to the backward-moving wire,
wherein the one or more coupling members are to move the operation member backward toward a proximal end of the one jaw while moving toward the proximal end of the one jaw together with the backward-moving wire.

2. The surgical instrument of claim 1,
wherein the one jaw further includes a backward-moving wire pulley disposed at the distal end of the one jaw,
wherein the backward-moving wire is wound to be in partial contact with the backward-moving wire pulley, the backward-moving wire having two strands extending toward the proximal end of the one jaw.

3. The surgical instrument of claim 2,
wherein the one jaw further includes an auxiliary pulley disposed adjacent to the backward-moving wire pulley,
wherein the auxiliary pulley is configured to adjust a position or a distance between the two strands of the backward-moving wire to arrange the backward-moving wire.

4. The surgical instrument of claim 2,
wherein the two strands of the backward-moving wire have an inner side wire, which is one of the two strands and closer to the operation member, and an outer side wire, which is another one of the two strands,
wherein the one or more coupling members are coupled to the outer side wire.

5. The surgical instrument of claim 2,
wherein the end tool further includes:
a jaw rotation shaft to serve as a rotation center of the one jaw; and
a loop pulley to which the jaw rotation shaft is coupled,
wherein the backward-moving wire is wound around the loop pulley to be in partial contact.

6. The surgical instrument of claim 5,
wherein the loop pulley comprises two pulleys that are independently rotatable, and
wherein the two strands of the backward-moving wire are respectively wound around the two pulleys of the loop pulley in different directions with respect to the jaw rotation shaft.

7. The surgical instrument of claim 2, wherein the reciprocating assembly has a plurality of recesses defined on at least one surface of the reciprocating assembly, wherein the operation member includes a ratchet member having a ratchet defined on at least one surface of the ratchet member, and wherein the ratchet of the ratchet member is configured to be in contact with each of the plurality of recesses of the reciprocating assembly.

8. The surgical instrument of claim 7, wherein the one or more coupling members are configured to contact the ratchet member to move the operation member backward toward the proximal end of the one jaw.

9. The surgical instrument of claim 8, wherein the ratchet member includes a protrusion protruding from an opposite surface of the at least one surface on which the ratchet is defined, and wherein the one or more coupling members are configured to contact the protrusion of the ratchet member.

10. The surgical instrument of claim 9, wherein the protrusion of the ratchet member forms a hollow, and wherein the backward-moving wire is configured to pass through the protrusion through the hollow.

11. The surgical instrument of claim 7, wherein the backward-moving wire and the one or more coupling members are positioned on an opposite side of the reciprocating assembly with respect to the ratchet member.

12. The surgical instrument of claim 2, wherein as the operation member moves forward toward the distal end, the one or more coupling members are configured to be moved together with the operation member at a front surface of the operation member while being spaced apart from the operation member to secure a clearance space.

13. The surgical instrument of claim 1, wherein the one or more coupling members are configured to be disposed on a distal end side of the one jaw to avoid interference with the operation member until the operation member moves forward to an end of the distal end of the one jaw.

14. A surgical instrument comprising:

an end tool including one or more jaws and rotatable in at least one direction, wherein one jaw of the one or more jaws includes:

a reciprocating assembly disposed in the one jaw and movable in a first direction, which is a longitudinal direction of the one jaw, with respect to the one jaw;

an operation member disposed on one side of the reciprocating assembly, the operation member being capable of contacting the reciprocating assembly and movable forward toward a distal end of the one jaw from a proximal end side of the one jaw in the first direction by the reciprocating assembly; and a backward-moving wire disposed adjacent to the operation member and movable in the first direction, wherein the backward-moving wire includes one or more coupling members fixed to the backward-moving wire, and wherein, when the reciprocating assembly moves toward the distal end of the one jaw, the one or more coupling members are configured to contact the operation member to prevent the operation member from moving toward a proximal end of the one jaw.

15. The surgical instrument of claim 14, wherein as the operation member moves forward toward the distal end, the one or more coupling members are configured to be moved together with the operation member at a rear surface of the operation member while being spaced apart from the operation member to secure a clearance space.

16. The surgical instrument of claim 14, wherein as the operation member moves forward toward the distal end, the one or more coupling members are configured to be moved together with the operation member at a rear surface of the operation member while applying a force to the operation member in a forward movement direction.

17. The surgical instrument of claim 14, wherein the operation member includes a protrusion protruding toward the backward-moving wire, wherein the one or more coupling members are disposed at a rear of the protrusion.

18. The surgical instrument of claim 14, wherein the reciprocating assembly has a plurality of recesses defined on at least one surface of the reciprocating assembly, wherein the operation member includes a ratchet member having a ratchet defined on at least one surface of the ratchet member, and wherein the ratchet of the ratchet member is configured to be in contact with the plurality of recesses of the reciprocating assembly.

19. The surgical instrument of claim 18, wherein the one or more coupling members are disposed at a rear of the ratchet member.

20. The surgical instrument of claim 19, wherein a protrusion of the ratchet member forms a hollow, and wherein the backward-moving wire is configured to pass through the protrusion through the hollow.

21. The surgical instrument of claim 14, wherein the backward-moving wire has two strands, the two strands comprising an inner side wire, which is one of the two strands and closer to the operation member, and an outer side wire, which is another one of the two strands, wherein the one or more coupling members are coupled to the inner side wire.

22. The surgical instrument of claim 14, wherein the backward-moving wire further includes a backward-movement coupling member configured to move the operation member backward toward the proximal end of the one jaw while moving toward the proximal end together with the backward-moving wire.

23. The surgical instrument of claim 22, wherein two strands of the backward-moving wire have an inner side wire, which is one of the two strands and closer to the operation member, and an outer side wire, which is another one of the two strands, wherein the backward-movement coupling member and the one or more coupling members are both coupled to the inner side wire or the outer side wire.

24. The surgical instrument of claim 23, wherein as the operation member moves forward toward the distal end, the backward-movement coupling member is configured to be moved together with the operation member at a front surface of the operation member while being spaced apart from the operation member to secure a clearance space.

* * * * *